US012767992B2

(12) United States Patent
Lamendella et al.

(10) Patent No.: US 12,767,992 B2
(45) Date of Patent: Oct. 20, 2026

(54) RAPID ISOLATION AND COLLECTION OF MICROBIAL RNA FROM A BIOLOGICAL SPECIMEN

(71) Applicant: CONTAMINATION SOURCE IDENTIFICATION INC., Hershey, PA (US)

(72) Inventors: Regina Lamendella, Hershey, PA (US); Justin Wright, Hershey, PA (US); Alexander Shope, Hershey, PA (US)

(73) Assignee: CONTAMINATION SOURCE IDENTIFICATION INC., Hershey, PA (US)

( * ) Notice: Subject to any disclaimer, the term of this patent is extended or adjusted under 35 U.S.C. 154(b) by 1059 days.

(21) Appl. No.: 17/638,111

(22) PCT Filed: Aug. 28, 2020

(86) PCT No.: PCT/US2020/070482

§ 371 (c)(1),
(2) Date: Feb. 24, 2022

(87) PCT Pub. No.: WO2021/042135

PCT Pub. Date: Mar. 4, 2021

(65) Prior Publication Data

US 2022/0290212 A1 Sep. 15, 2022

Related U.S. Application Data

(60) Provisional application No. 62/892,821, filed on Aug. 28, 2019.

(51) Int. Cl.

| | |
|---|---|
| ***C12Q 1/689*** | (2018.01) |
| ***B01D 15/16*** | (2006.01) |
| ***B01D 15/24*** | (2006.01) |
| ***B01D 15/34*** | (2006.01) |
| ***B01D 15/42*** | (2006.01) |
| ***C12Q 1/6806*** | (2018.01) |

(52) U.S. Cl.

CPC .......... *C12Q 1/689* (2013.01); *B01D 15/166* (2013.01); *B01D 15/24* (2013.01); *B01D 15/34* (2013.01); *B01D 15/426* (2013.01); *C12Q 1/6806* (2013.01)

(58) Field of Classification Search

None

See application file for complete search history.

(56) References Cited

U.S. PATENT DOCUMENTS

| | | | |
|---|---|---|---|
| 5,258,302 A | 11/1993 | Vedvick et al. | |
| 8,313,931 B2 | 11/2012 | Miller | |
| 8,383,340 B2 | 2/2013 | Ketterer et al. | |
| 9,062,303 B2 | 6/2015 | Chen et al. | |
| 9,435,739 B2 | 9/2016 | Roscoe et al. | |
| 10,077,439 B2 | 9/2018 | Issa et al. | |
| 2005/0014128 A1 | 1/2005 | Ewert et al. | |
| 2005/0123928 A1* | 6/2005 | Das | C07H 21/04 435/6.13 |
| 2006/0057616 A1* | 3/2006 | Montagnier | C12Q 1/689 435/6.16 |
| 2013/0196415 A1* | 8/2013 | Doi | B09B 3/00 435/267 |
| 2016/0108463 A1 | 4/2016 | Fischer et al. | |
| 2017/0219577 A1 | 8/2017 | Percy et al. | |

FOREIGN PATENT DOCUMENTS

| | | |
|---|---|---|
| GB | 2581489 A | 8/2020 |
| JP | 2005/052142 A | 3/2005 |
| JP | 2005-151975 A | 6/2005 |
| WO | WO-2008/077592 A1 | 7/2008 |
| WO | 2020/165602 A1 | 8/2020 |
| WO | WO-2021/042135 A2 | 3/2021 |

OTHER PUBLICATIONS

Persson et al. Purification of RNA-DNA hybrids by exclusion chromatography. J Biol Chem. Aug. 25, 1979; 254(16): 7999-8003). (Year: 1979).*

Pager et al: A Liquid Chromatographic Preparation of Retroviral RNA, Analytical Biochemistry, Academis Press, Amsterdam, NL, vol. 215, No. 2, Dec. 1, 1993 (Dec. 1, 1993), pp. 231-235, XP024763436, ISSN: 0003-2697, DOI: 10.1006/ABIO.1993.1580.

Nwokeoji Alison O et al: "RNASwift: A rapid, versatile RNA extraction method free from phenol and chloroform", Analytical Biochemistry, Academic Press, Amsterdam, NL, vol. 512, Aug. 3, 2016 (Aug. 3, 2016), pp. 36-46, XP029711378, ISSN: 0003-2697, DOI: 10. 1016/J.AB.2016.08.001.

Mclaughlin L W Ed-Chamkvetadze B et al: "Resolution of RNA using high-performance liquid chromatography", Journal of Chromatography A, Elsevier, Amsterdam, NL, vol. 418, Jan. 1, 1987 (Jan. 1, 1987), pp. 51-27, XP002112449, ISSN: 0021-9673.

Written Opinion of the ISA for PCT/US2020/070482, filed Aug. 28, 2020, mailed Feb. 17, 2021, 5 pages.

(Continued)

*Primary Examiner* — Robert A Wax
*Assistant Examiner* — Julia A. Rossi
(74) *Attorney, Agent, or Firm* — Foley Hoag LLP; Matthew D. Jonsen; Maya Elbert

(57) ABSTRACT

Detection and identification of microbial species uses liquid chromatography as a bulk filtration process for rapid isolation and collection of microbial RNA from a biological specimen. In various embodiments, gene sequencing of microbial RNA molecules from a biological specimen is enhanced by obtaining and then preparing the biological specimen as a test sample for liquid chromatography that is used to bulk filter microbial RNA molecules from a mixture of RNA molecules in the test sample to isolate and collect the microbial RNA molecules in two or more fraction outputs, wherein at least one of the two or more fraction outputs is a fraction within a void volume of the liquid chromatography, preparing one or more fraction outputs for gene sequencing, including the fraction output that is within the void volume, and conducting gene sequencing on the one or more prepared outputs to detect microbial RNA from the biological specimen.

15 Claims, 10 Drawing Sheets

(56) References Cited

OTHER PUBLICATIONS

International Preliminary Report on Patentability for PCT/US2020/070482, filed Aug. 28, 2020, dated Mar. 1, 2022, 6 pages.
Persson et al. "Purification of RNA-DNA Hybrids by Exclusion Chromatography," The Journal of Biological Chemistry, Aug. 25, 1979 (Aug. 25, 1979), vol. 254, No. 16, pp. 7999-8003. entire document.
3M™ Molecular Detection System (incubation for up to 30 hours as described in links available at https://multimedia.3m.com/mws/media/1353351O/3m-moleular-detection-assay-2-1-monocytogenes-update.pdf, 262 pages.
Tan et al, "DNA, RNA, and Protein Extraction: The Past and The Present" Hindawi Publishing Corporation Journal of Biomedicine and Biotechnology vol. 2009, Article ID 574398, 10 pages, doi:10.1155/2009/574398.
Turbo™ DNase, (2 U/μL) Invitrogen™ Catalog No. AM2238, available from ThermoFisher.
Brennecke et al., „High-yield extraction of *Escherichia coli* RNA from human whole Blood, J Med Micro, 2017, 66: 301, 11 pages. https://www.wrightlabs.org/metatranscriptomics_2, 4 pages.
Hao Qin et al., "Comparative transcriptomics of multidrug-resistant *Acinetobacter baumannii* in response to antibiotic treatments", Scientific Reports, Feb. 23, 2018, 11 pages, also available at https://www.nature.com/articles/s41598-018-21841-9.
Ariane Khaledi et al., "Transcriptome Profiling of Antimicrobial Resistance in Pseudomonas aeruginosa", Antimicrobial Agents and Chemotherapy, Aug. 2016 vol. 60 No. 8, pp. 4722-4733.
Table of Contents for Molecular Cell Biology, $4^{th}$ ed, Lodish, et al, W.H. Freeman, 1999.
Table of Contents for Bioanalytical Chemistry, $2^{nd}$ ed, Manz et al, Imperial College Press, 2015.
Table of Contents for Principles of Instrumental Analysis, $5^{th}$ ed, Skoog and Holler, Harcourt Brace, 1998.
Stewart, D.B.; Write, J.R.; Fowler, M.; McLimans, C.J.; Tokarev, V.; Amaniera, I.; Baker, O.; Wong, H.; Brabec, J.; Drucker, R.; Lamendella, R. "Integrated Meta Omics Reveals a Fungus-Associated Bacteriome and Distinct Functional Pathways in *Clostridioides difficile* Infection", Clinical Science and Epidemiology, 4(4), 1-16.
Goswami, K.; Purtill, J.J.; Shope, A.J.; Wright, J.; Lamendella, R. Shotgun Metatranscriptomics for PJI diagnosis: A Novel Prospective Investigation, 2019 Abstract submission, AAHKS Annual Meeting.
Goswami, K.; Purtill, J.J.; Shope, A.J.; Wright, J.; Lamendella, R. Shotgun Metatranscriptomics for PJI diagnosis: A Novel Prospective Investigation, 2019 Slide deck presentation, AAHKS Annual Meeting.
Slide deck for CSI Compendium, Confidential Investor Presentation, unpublished work (2019).

* cited by examiner

RAPID ISOLATION AND COLLECTION OF MICROBIAL RNA FROM A BIOLOGICAL SPECIMEN

RELATED APPLICATIONS

This application is a National Phase entry of PCT Application No. PCT/US2020/070842 filed Aug. 28, 2020, which application claims the benefit of priority to U.S. Provisional Application No. 62/892,821 filed Aug. 28, 2019, the entire disclosures of which are incorporated herein by reference.

TECHNICAL FIELD

The present disclosure relates to the separation of nucleic acids from biological specimens. More particularly, the present disclosure relates to more efficient and effective detection and identification of microbial species by using liquid chromatography as a bulk filtration process for the rapid isolation and collection of microbial RNA from a biological specimen.

BACKGROUND

Detection and identification of microbial species is important for diagnosing and treating disease, and for identifying source contamination and preventing infection in various clinical, environmental or production contexts. Microbial species can include bacteria, viruses, protozoa, fungi, algae, amoebas, and slime molds.

Detection and identification of specific microbial species can be useful in the evaluation and treatment of patients and products, as well as facilities and environments, such as medical-related facilities like hospitals or clinics and food production environments like manufacturing plants or kitchens. Detection of specific microbial species is used, for example, in medical offices, in order to determine the presence and identity of pathogens causing infection to a patient, thus allowing for appropriate treatment and remedy. The same methods are used in healthcare, the food industry, and long-term care industry, hospitality industry, homeland security, aerospace and aviation, and even in the private sector.

Unfortunately, detection of microbial species from biological specimens obtained from such clinical, environmental or production contexts differ from detection of microbial species in controlled biological samples that are used in theoretical or research contexts. The raw biological specimens from such clinical, environmental or production contexts are not controlled or refined, and the time and expense that can be spent to obtain useable results from a biological sample in a theoretical or research context are significantly more than can be spent on obtaining results from a biological specimen in a clinical, environmental or production context.

Biological specimens are uniquely complex and can include biological materials that range from urine and feces to whole blood and serum to intact tissue. Biological specimens may comprise lipids, proteins, nuclear and mitochondrial DNA, RNA (i.e. tRNA, rRNA, mRNA), and will contain all of the above macromolecules for both the mammalian source of the specimen as well as any single-celled organisms (i.e. microbial species) that are present in the sample and infecting the host organism. Typically, biomarkers of a pathogen (e.g. DNA and RNA) are present at a significantly lower level than that of the source of the biological specimen, making isolation and detection difficult. Current techniques for microbial detection in the theoretical and research context rely on incubation and/or purification techniques applied to biological specimens in order to form relevant and actionable biological samples suitable for genetic analysis.

Incubation techniques can take up to 30 hours before the specimen can be analyzed thereby delaying the ability to act upon the results of detection of specific microbial species to achieve a favorable and timely outcome. Examples of such incubation techniques used to amplify genetic sequences are described, for example, in U.S. Pat. Nos. 8,313,931 (incubation for 20 hours) and 9,435,739 (incubation for 18-24 hours), and for the 3M™ Molecular Detection System (incubation for up to 30 hours as described in links available at https://multimedia.3m.com/mws/media/1353351O/3m-molecular-detection-assay-2-1-*monocytogenes*-update.pdf and U.S. Publ. Appl. No. 2017/0219577 A1).

Purification techniques to isolate and detect biomarkers of microbial species by filtration, elution, or binding techniques as described, for example, in U.S. Pat. Nos. 9,062,303 and 8,383,340. Chaotropic agents such as DNase have been used to degrade proteins other than RNA in a clinical sample (Tan et al, J Biomed and Biotech, 2009, Turbo Dnase, available from ThermoFisher, U.S. Pat. No. 10,077,439); however, these methods do not allow for isolation of microbial RNA from non-microbial RNA. Similarly, methods to extract *E. coli* from human blood using copurification with different lysis buffers have been disclosed (Brennecke et al, J Med Micro, 2017, 66: 301), but these methods rely on first extracting the target RNA from the biological specimen, and then degrading and removing any residual DNA. The use of specially prepared sterile plates to isolate specific strains of bacteria have been used in a research context to obtain relevant and actionable biological samples of each bacteria strain suitable for genetic analysis. See, material in links available at https://www.wrightlabs.org/metatranscriptomics_2, https://aac.asm.org/content/60/8/4722, https://www.nature.com/articles/s41598-018-21841-9. Unfortunately, these kinds of purification techniques require further processing and manipulation of the biological specimens, which may result in degradation of the genetic biomarkers of interest.

Various methods and systems for the detection of microbial DNA, particularly in the theoretical or research context are also known in the art. However, these techniques rely on detection of microbial DNA and cannot distinguish between the presence of live or dead microbial species. Moreover, because other kinds of DNA in a biological specimen typically overwhelm the relative amount of microbial DNA in that biological specimen, detection of microbial DNA using conventional DNA identification requires incubation or preparation of a biological sample in which sufficient numbers of the microbial species of interest are grown to reliably detect and identify those microbes.

There exists a need for a technique that can rapidly isolate and detect biomarkers of microbial species from biological specimens without significant, intentional, incubation or purification in order to facilitate more effective, efficient and rapid identification of microbial species in such biological specimens for the evaluation and treatment of patients and products, as well as facilities and environments.

SUMMARY

One aspect of the present disclosure is a method for rapidly transforming a biological specimen into a microbial RNA filtered sample by bulk filtration without degrading microbial RNA that are biomarkers of pathogenic organisms by using the void volume in a liquid chromatography process in order to enhance the efficiency by which the presence of such pathogenic organisms may be detected by subsequent genetic sequencing techniques.

Another aspect of the present disclosure relates to a method for rapidly filtering a test sample obtained from a biological specimen to isolate and collect microbial RNA, a biomarker of live or viable microbial species, in which the method is substantially free of a step designed to intentionally grow genetic material. In various embodiments, the present disclosure comprises the steps of obtaining a biological specimen, digesting or preparing the biological specimen to create a test sample to allow for liquid chromatography, and using bulk filtration by liquid chromatography to isolate and collect microbial RNA molecules from the test sample.

In some aspects of the present invention, the method for rapidly filtering a test sample obtained from a biological specimen to isolate and collect microbial RNA eliminates a step of incubating or purifying genetic material by using liquid chromatography to bulk filter microbial RNA molecules from a mixture of RNA molecules that includes host RNA molecules by only using the void volume output of the liquid chromatography in order to effectively amplify the microbial RNA molecules from the test sample relative to the host RNA molecules.

In one embodiment, a method for filtering microbial RNA molecules from a biological specimen to isolate microbial RNA includes the steps of: (a) obtaining the biological specimen; (b) digesting the biological specimen to create a test sample by interacting a reagent with the specimen; and (c) using liquid chromatography to bulk filter microbial RNA molecules from a mixture of RNA molecules in the test sample to isolate and collect the microbial RNA molecules from the test sample.

In one embodiment, a method of filtering a microbial single-stranded nucleic acid sequence from a mixture of one of at least a mammalian single-stranded nucleic acid sequence and a microbial single-stranded nucleic acid sequence is performed by collecting microbial RNA molecules from a void volume of a liquid chromatography method, wherein the microbial single-stranded nucleic acid sequence is a catalyst for synthesis of a protein. In one embodiment, a method for filtering microbial RNA molecules from a biological specimen to isolate microbial RNA comprises obtaining the biological specimen; preparing the biological specimen to create a test sample by interacting a reagent with the specimen; and using a liquid chromatography instrument to bulk filter microbial RNA molecules from a mixture of RNA molecules in the test sample to isolate and collect the microbial RNA molecules from the test sample a void volume of the liquid chromatography instrument.

In some aspects, a flow rate of the liquid mobile phase is about 0.5 mL/min. to about 3.5 mL/min., in some aspects about 550 μL/min. to about 2 mL/min., in some aspects about 600 μL/min. to about 1 mL/min., and in some other aspects about 650 μL/min. to about 850 μL/min.

In some aspects, the void volume has a retention time of between greater than 0 seconds and less than about 6 minutes, in some aspects less than about 5 minutes, in some aspects less than about 4 minutes, in some aspects less than about 3 minutes, and in some other aspects less than about 2 minutes.

In some aspects, a plurality of fractions of mobile phase with any filtered sample material are eluted using liquid chromatography and collected for a period of time between about 5 seconds and about 1 minute, in some aspects between about 10 seconds and about 45 seconds, and in some aspects about 15 seconds and about 30 seconds, wherein each aliquot comprises between about 100 μL to about 1 mL, in some aspects between about 125 μL to about 750 μL, in some aspects between about 150 μL to about 500 μL, and in some aspects between about 175 μL to about 250 μL.

In one embodiment, microbial RNA is detected from one or more fractions eluted using liquid chromatography, wherein the microbial RNA is detected using gene sequencing on one or more of the fractions. In some aspects, the one or more fractions comprises one or more fractions of the void volume eluted using liquid chromatography, wherein the microbial RNA is detected using gene sequencing on one or more fractions comprising the void volume.

In some aspects, each fraction is subjected to dehydration prior to gene sequencing, wherein each aliquot is dehydrated to a volume between about 15 μL and about 500 μL, in some aspects between about 20 μL and about 100 μL, in some aspects between about 25 μL and about 75 μL, and in some preferred aspects between about 35 μL and about 65 μL.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1:
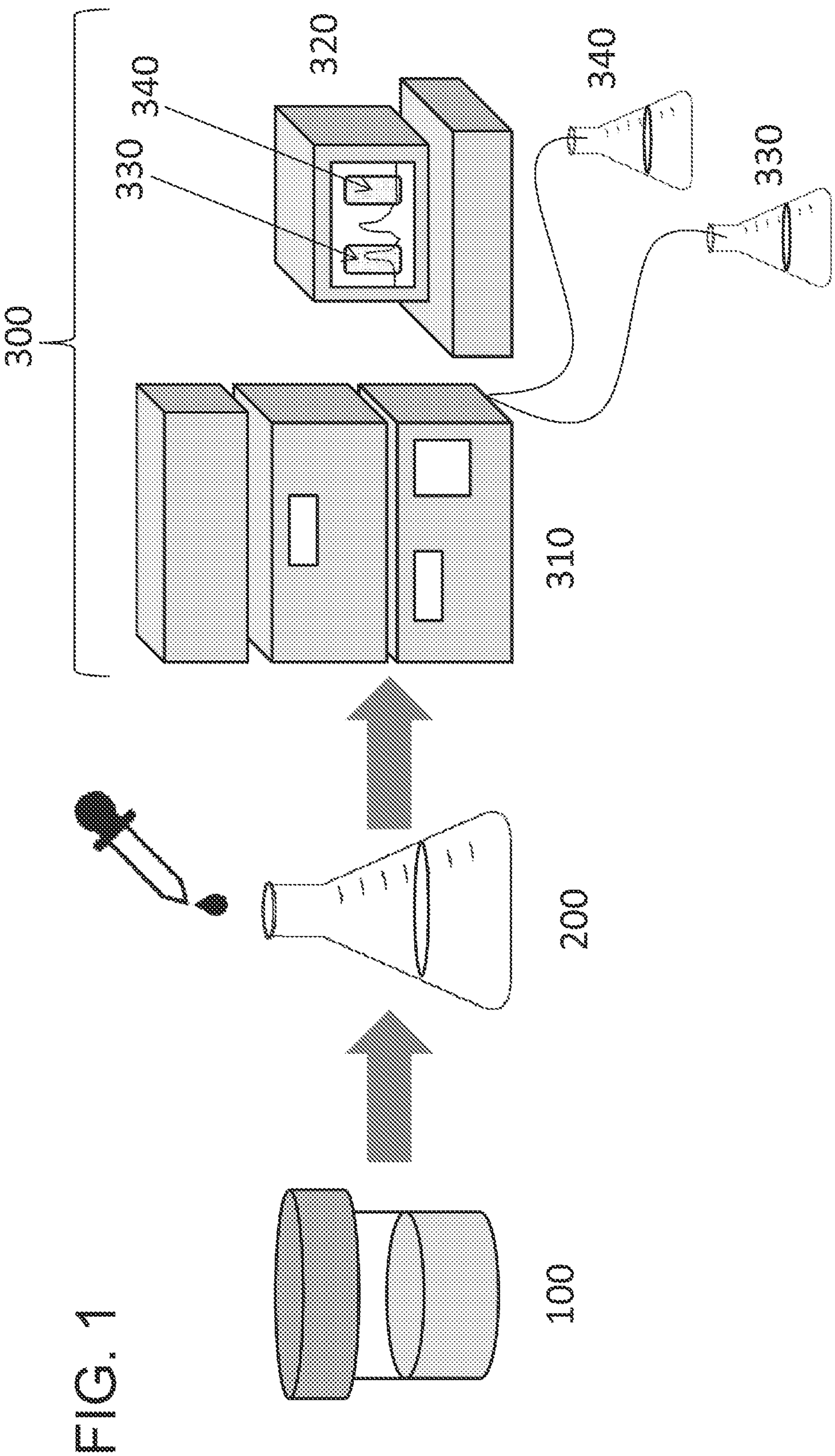
FIG. 1 shows a representative workflow diagram of one embodiment of a bulk filtration method in accordance with the present invention.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

In describing the various embodiments set forth in this disclosure, the following definitions and conventions are used in understanding the disclosure of the various embodiments. In understanding this disclosure, it will be recognized that the disclosure describes various embodiments that integrate or combine certain techniques and equipment used by microbiologists with those used by analytical chemists. The following definitions and convention provide a common set of terminology that is useful and helpful in understanding the disclosure because these two areas of microbiologists and analytical chemists may not have consistent understandings or usages of terminology.

The terms "mammalian", "non-microbial species", or "non-microbial population" are understood to encompass all species that are not bacterial, viral, fungal, or yeast populations or combinations thereof or any mixture thereof in a laboratory or natural setting, and that are comprised of multi-cellular organisms.

The terms "microbial", "microbial population", or "microbial species" are understood to encompass bacterial, viral, fungal, or yeast populations or combinations thereof or any mixture thereof in a laboratory or natural setting, and that are comprised of single-celled organisms.

The term "biological specimen" refers to raw biological specimens that are untreated and sourced from mammalian species, including whole blood, plasma, mucus, serum, urine, feces, intact tissue, cerebrospinal fluid, synovial fluid; environmental swabs; food sources; and unknown powders obtained from a surface. Thus, reference to a biological specimen may include reference to one or more of the aforementioned sources.

The term "test sample" refers to a biological specimen following preparation or pre-treatment for introduction to a liquid chromatography instrument, that may include execution of steps that remove proteins, deoxyribonucleic acid (DNA), lipids, and other macromolecules.

The term "double stranded nucleic acid sequence" refers to DNA.

The term "single stranded nucleic acid sequence" refers to "ribonucleic acid", or "RNA", and is understood to encompass transfer RNA (tRNA), ribosomal RNA (rRNA), messenger RNA (mRNA), large RNA, small RNA, denatured and non-denatured RNA, fragmented and intact RNA.

The term "liquid chromatography", "HPLC", "HPLC instrument", and the like are synonyms that refer to the machine, instrument and/or techniques used to isolate and collect microbial RNA from non-microbial RNA in accordance with various embodiments.

The terms percent (%), weight percent (% w/w), weight-volume percent (% w/v), % by weight, % by volume, and the like are synonyms that refer to the concentration of a substance as the weight of that substance divided by the total weight or volume at standard room temperature and pressure, multiplied by 100.

The term "about" modifying the quantity of an ingredient in the compositions of the disclosure, or times employed in the method of the disclosure refers to the variation in the numerical quantity that can occur, for example, through typical measuring and handling procedures for making concentrates or solutions in the real world; through inadvertent errors in procedures; through differences in the manufacture, source, or purity of the ingredients employed to make these compositions and methods; through differences in instrument (machine) settings.

The term "about" also encompasses amounts that differ due to different equilibrium conditions for a composition resulting from a particular initial mixture. Whether or not modified by the term "about", the claims include equivalents to the quantities. Other than in the operating examples, or otherwise whereas indicated, all numbers expressing quantities of ingredients or reaction conditions used herein are to be understood as being modified in all instances by the term "about".

The central dogma of molecular biology explains that information may be passed from nucleic acid to nucleic acid, or from nucleic acid to protein, but information transfer from protein to protein, or from protein to nucleic acid, is not possible. Within both mammalian and microbial systems, RNA is a nucleic acid sequence that is responsible for either synthesizing proteins, transporting amino acids for synthesis, or catalyzing the synthesis of proteins. The present disclosure capitalizes on the fact that RNA is a transitional molecule between DNA and proteins and makes use of bulk filtration of microbial RNA as a means of identifying species of interest and function of proteins within a biological sample.

RNA comes in three "types", referred to as mRNA, tRNA, and rRNA. mRNA is responsible for protein synthesis, tRNA is responsible for transporting amino acids for synthesis, and rRNA is responsible for catalyzing, or initiating, protein synthesis. mRNA is often studied because it is comparatively larger than fragments of rRNA, and is directly responsible for coding proteins. From an information perspective, mRNA has historically been viewed as being most meaningful to scientific study.

Despite interest in RNA, this class of molecules is difficult to analyze. Unlike DNA, which can last for millions of years in ideal conditions, RNA typically degrades within minutes of the death of an organism. However, because of its short half-life, the detection of RNA typically indicates the presence of an organism that, at the time of analysis, was viable.

Traditional molecular biology or biochemical techniques rely on strategies including, but not limited to: Enzyme Linked Immunosorbent Assay (ELISA), Polymerase Chain Reaction (PCR), Acid Guanidinium Thiocyanate-Phenol- Chloroform extraction (AGPC), and liquid-liquid extraction to isolate RNA molecules from a complex biological system. (Molecular Cell Biology, $4^{th}$ ed, Lodish, et al, W.H. Freeman, 1999). However, a key limitation of these techniques is that RNAase present in the samples may degrade RNA molecules of interest. Moreover, prior knowledge of the target RNA structure is needed to leverage both ELISA and PCR techniques. (Bioanalytical Chemistry, $2^{nd}$ ed, Manz et al, Imperial College Press, 2015). While AGPC and liquid-liquid extraction may isolate RNA molecules, these techniques isolate all RNA, regardless of type or species of interest.

In contrast to traditional molecular biology or biochemical techniques, traditional analytical chemistry techniques were developed to be applied to the analysis of small molecules and have not traditionally been suitable to the analysis of nucleic acids or other biopolymers. (Bioanalytical Chemistry, $2^{nd}$ ed, Manz et al, Imperial College Press, 2015)

A hybrid technology arena has developed, namely bioanalytical chemistry, that addresses the unique challenges of the analysis of large, complex, biological molecules, which include RNA. The use of 2-Dimensional Polyacrylamide Gel Electrophoresis (2D-PAGE) gels, Matrix-Assisted Laser Desorption/Ionization-Time of Flight (MALDI-TOF), capillary electrophoresis, and biosensors, have all allowed for quantitation, structural elucidation, and qualitative analysis and isolation of biological molecules of interest with a higher degree of specificity and speed than traditionally found in molecular biology and biochemical strategies.

With these bioanalytical methods, High Performance Liquid Chromatography (HPLC) has been adapted to allow for analysis of large biological molecules. (Principles of Instrumental Analysis, $5^{th}$ ed, Skoog and Holler, Harcourt Brace, 1998). HPLC relies on chemical separation of mixtures based on an interaction between a column (referred to as the stationary phase) and a liquid (referred to as a mobile phase). Typical HPLC columns are made of a steel outer shell packed with polystyrene or silanol microbeads and, as mobile phase containing a sample of interest is pumped through the column, the components of the sample (a mixture) partition into and out of the stationary phase. The more the components "like" the stationary phase, the more these components are retained and the longer the components take to exit, or elute from, the column. As components are detected, each is assigned a "retention time" on a plot referred to as a "chromatogram". Each column has a "$t_0$", which refers to all molecules that are not retained by the column in what is referred to as the "void volume". The void volume is largely regarded by chromatographers as informatically irrelevant; because this region of a chromatogram contains mixtures of molecules that were not chemically separated, this region of a chromatogram is traditionally unutilized, and molecules found in this region are traditionally not studied or of interest.

In some aspects of the present invention, the void volume represents a time from when the sample is introduced in the column using liquid chromatography up to a period of time of about 6 minutes, in some aspects up to about 5 minutes, in some aspects up to about 4 minutes, in some aspects up to about 3 minutes, and in some other aspects up to about 2 minutes, wherein the flow rate of the mobile phase is between about 0.5 mL/min. to about 3.5 mL/min., in some aspects between about 550 μL/min. to about 2 mL/min., in some aspects between about 600 μL/min. to about 1 mL/min., and in some other aspects between about 650 μL/min. to about 850 μL/min.

Within bioanalysis, there are two modes of HPLC that are common: Reverse Phase Liquid Chromatography (RPLC) and Ion Exchange Liquid Chromatography (IE-LC). RPLC has a column that is packed with a hydrophobic stationary phase, and molecules elute from the column according to both size and polarity. Hydrophobic molecules are retained for extended periods of time, and hydrophilic molecules are largely unretained. The most hydrophobic molecules elute in the void volume of the column. Within RPLC, the void volume is made of a mixture of one or more hydrophilic molecules of various sizes that failed to interact with the column stationary phase.

Unlike RPLC, IE-LC chemically separates molecules according to a net, overall, charge. The column stationary phase is made of microspheres with a net positive charge, and molecules are adsorbed onto the column stationary phase, and desorbed from it, when there is an increase in salt content or pH for the mobile phase. Molecules elute from the column and are detected. Using IE-LC, molecules with an increasing size or increasing negative charge are retained the longest and take the longest to elute from the column; in contrast, electrically neutral molecules or those with a positive charge elute in the void volume. This approach has been used previously to chemically separate mRNA from a mixture of total RNA; this approach, however, has never investigated or leveraged the void volume as a means of RNA collection.

Traditionally, mRNA has been most studied because it is comparatively larger than fragments of rRNA, which allows scientists to obtain information more accurately and quickly. Such traditional approaches for analysis of mRNA have removed and discarded rRNA and tRNA, rather than reserving these types of RNA for subsequent analysis. Unlike such traditional approaches, the various embodiments of the present disclosure capitalize on the central dogma of molecular biology to rapidly filter and isolate, rather than chemically separate, microbial RNA, with particular emphasis on rRNA for further bioinformatic study by collecting all RNA fragments found in the void volume of a liquid chromatography process.

The present disclosure relates to a method for rapidly filtering a test sample obtained from a biological specimen to isolate and collect microbial RNA, a biomarker of live or viable microbial species, in which the method is substantially free of a step designed to intentionally grow genetic material. In various embodiments, the present disclosure comprises the steps of obtaining a biological specimen, digesting or preparing the biological specimen to create a test sample to allow for chromatography, and using bulk filtration by liquid chromatography to isolate and collect microbial RNA molecules from the test sample.

In some aspects of the present invention, the method of the present invention eliminates the need to incubate or purify genetic material by using liquid chromatography to bulk filter microbial RNA molecules from a mixture of RNA molecules, such as RNA molecules from the host from which the biological sample is obtained, in order to amplify the microbial RNA molecules from the test sample. As such, in some aspects, the method of the present invention is devoid of the step of incubating the test sample to grow genetic material by only using the void volume output of the liquid chromatography in order to effectively amplify the microbial RNA molecules. In some aspects, the method of the present invention is devoid of the step of purifying the test sample by only using the void volume output of the liquid chromatography in order to effectively amplify the microbial RNA molecules.

As described in FIG. 1, a clinical specimen 100 is obtained. In one embodiment, a clinical specimen is an environmental swab from a hard surface, wherein the swab is extracted in a buffered solution in a test vial. Buffered solutions may be comprised of 0.1× to 2.5× phosphate buffered saline (PBS), 0.05M to 1.5M Peptone water, or 30% to 50% guanidine hydrochloride with 0.1% to 1% maleic acid.

In another embodiment, a biological specimen is a tissue or excretion from a mammalian species, including but not limited to humans and domesticated animal species. The biological specimen includes, but is not limited to, whole blood, plasma, mucus, serum, urine, feces, cerebrospinal fluid, synovial fluid, and intact tissue. Clinical specimens may be obtained by blood draw, punch biopsy, stool culture, nasal swab, saliva sample, urinalysis, dermatology scraping, in addition to any other established protocol for collecting a specific form of biological specimen. Biological specimens contain large RNA molecules, small RNA molecules, tRNA molecules, rRNA molecules, mRNA molecules, denatured and non-denatured RNA molecules, microbial RNA molecules, non-microbial RNA molecules, genomic DNA molecules, protein molecules, and other macromolecules.

The biological specimen may be mechanically homogenized, cavitated by nitrogen, or sonicated, as appropriate using methods known in the art to prepare the specimen for the subsequent step of digesting in order to create a test sample. The biological specimen then undergoes the step of digesting 200. Digesting the clinical specimen may include enzymes, chaotropes, surfactants, detergents, and other additives known in the art. The process of digesting the biological specimen removes genomic DNA molecules, protein molecules and non-RNA macromolecules, and may occur at low temperatures to prevent degradation of the biological specimen and may optionally include additives known to preserve target molecules, as described in Table 1.

TABLE 1

Additives for preservation of target molecules while digesting clinical specimens.

| Inhibitor | Specificity | Use Level | Preferred Embodiment |
|---|---|---|---|
| PMSF | Cysteine and serine proteases | 0.1 mM to 1 mM | Dissolve in ethanol before using. |
| EDTA | Metalloproteases | 0.5 mM to 1.5 mM | Use when divalent cations are in the specimen. |
| Pepstatin A | Acid proteases | 1 μM to 2 μM | Prepare at 1 mg/mL and dilute immediately before use. |
| Leupeptin | Serine and thiol proteases | 10 μM to 100 μM | Prepare 25 mg/mL and dilute immediately before use. |
| Aprotinin | Serine proteases | 0.1 μM to 0.8 μM | Use 1 mg/mL of 5 mg/mL stock solution. |

In one embodiment, digesting the biological specimen begins by lysing the clinical specimen by interacting the biological specimen with Guanidinium thiocyanate, N-Lauroylsarcosine, and ethanol. In one embodiment, a buffer solution of 55% to 85% Guanidinium thiocyanate and 1% to 20% N-Lauroylsarcosine is mixed in equal volumes with a solution of 70% to 100% ethanol. In one embodiment, a buffer solution of 65% to 75% Guanidinium thiocyanate and 1% to 10% N-Lauroylsarcosine is mixed in equal volumes with a solution of 70% to 100% ethanol. In still another embodiment, a buffer solution of 65% to 75% Guanidinium thiocyanate and 1% to 10% N-Lauroylsarcosine is mixed in equal volumes with a solution of 90% to 100% ethanol.

In one embodiment, digesting the biological specimen by lysing the specimen continues by adding 1 to 3 volumes of a buffer solution and ethanol mixture to a volume of a clinical specimen. In one embodiment, 2 volumes of the buffer solution and ethanol mixture are added to a volume of a clinical specimen. In another embodiment, 200 μL to 400 μL of a buffer solution and ethanol mixture are added to a volume of a clinical specimen. In one embodiment, 250 μL to 350 μL of a buffer solution and ethanol mixture are added to a volume of a clinical specimen.

The aforementioned mixture with the biological specimen is mixed either through manual inversion, vortexing, or other means known in the art, then transferred through a silica or polypropylene filter by centrifugation at 500 g to 2000 g for 15 seconds to 90 seconds. In one embodiment, 15 seconds to 45 seconds of centrifugation are used. The material that passes through the filter is discarded, and the DNA and RNA remaining on the filter are subjected to further preparative steps.

Once the biological specimen is digested, the next step of preparing and washing the biological specimen may include interacting the clinical specimen with one of at least Guanidinium chloride, ethanol, 2-amino-2-(hydroxymethyl)-propane-1,3-dihydrochloride, and edetate disodium. In one embodiment, a mixture of 70% to 100% ethanol containing 25% to 55% Guanidinium chloride is added to the same silica or polypropylene filter at a volume of 300 μL to 500 μL and centrifuged at 500 g to 2000 g for 15 seconds to 90 seconds. The material that passes through the filter is discarded. In another embodiment, a mixture of 12 mg/m$^3$ to 790 mg/m$^3$ 2-amino-2-(hydroxymethyl) propane-1,3-dihydrochloride, and 20 mg/m$^3$ to 2,000 mg/m$^3$ edetate disodium, is prepared and added to the same silica or polypropylene filter at a volume of 400 μL to 900 μL and centrifuged at 500 g to 2000 g for 15 seconds to 60 seconds. The material that passes through the filter is discarded. In yet another embodiment, a second mixture of 12 mg/m$^3$ to 790 mg/m$^3$ 2-amino-2-(hydroxymethyl) propane-1,3-dihydrochloride, and 20 mg/m$^3$ to 2,000 mg/m$^3$ edetate disodium, is prepared and added to the same silica or polypropylene filter at a volume of 400 μL to 900 μL and centrifuged at 500 g to 2000 g for 30 seconds to 180 seconds. In another embodiment, water is added to the same silica or polypropylene filter and centrifuged at 50 g to 2000 g for 15 seconds to 60 seconds. The material that passes through the filter is the biological specimen and is retained.

In one embodiment, a mixture of 80% to 100% ethanol containing 30 to 47% Guanidinium chloride is added to the same silica or polypropylene filter and centrifuged at 500 g to 2000 g for 15 seconds to 60 seconds. In yet another embodiment, a mixture of 90% to 100% ethanol containing 35 to 45% Guanidinium chloride is added to the same silica or polypropylene filter and centrifuged at 500 g to 2000 g for 15 seconds to 45 seconds. The material that passes through the filter is the biological specimen and is retained.

In another embodiment, a mixture of 25 mg/m$^3$ to 600 mg/m$^3$ 2-amino-2-(hydroxymethyl) propane-1,3-dihydrochloride, and 50 mg/m$^3$ to 1,000 mg/m$^3$ edetate disodium, is prepared and added to the same silica or polypropylene filter at a volume of 200 μL to 500 μL and centrifuged at 500 g to 2000 g for 15 seconds to 60 seconds. In yet another embodiment, a mixture of 25 mg/m$^3$ to 600 mg/m$^3$ 2-amino-2-(hydroxymethyl) propane-1,3-dihydrochloride, and 50 mg/m$^3$ to 1,000 mg/m$^3$ edetate disodium, is prepared and added to the same silica or polypropylene filter at a volume of 200 μL to 500 μL and centrifuged at 500 g to 2000 g for 15 seconds to 60 seconds. In yet another embodiment, a mixture of 25 mg/m$^3$ to 600 mg/m$^3$ 2-amino-2-(hydroxymethyl) propane-1,3-dihydrochloride, and 50 mg/m$^3$ to 1,000 mg/m$^3$ edetate disodium, is prepared and added to the same silica or polypropylene filter at a volume of 200 μL to 500 μL and centrifuged at 500 g to 2000 g for 15 seconds to 45 seconds.

In another embodiment, a second mixture of 25 mg/m$^3$ to 600 mg/m$^3$ 2-amino-2-(hydroxymethyl) propane-1,3-dihydrochloride, and 50 mg/m$^3$ to 1,000 mg/m$^3$ edetate disodium, is prepared and added to the same silica or polypropylene filter at a volume of 400 μL to 900 μL and centrifuged at 500 g to 2000 g for 30 seconds to 180 seconds. In yet another embodiment, a second mixture of 25 mg/m$^3$ to 600 mg/m$^3$ 2-amino-2-(hydroxymethyl) propane-1,3-dihydrochloride, and 50 mg/m$^3$ to 1,000 mg/m$^3$ edetate disodium, is prepared and added to the same silica or polypropylene filter at a volume of 600 μL to 800 μL and centrifuged at 500 g to 2000 g for 30 seconds to 180 seconds. In yet another embodiment, a second mixture of 25 mg/m$^3$ to 600 mg/m$^3$ 2-amino-2-(hydroxymethyl) propane-1,3-dihydrochloride, and 50 mg/m$^3$ to 1,000 mg/m$^3$ edetate disodium, is prepared and added to the same silica or polypropylene filter at a volume of 600 to 800 μL and centrifuged at 500 g to 2000 g for 90 seconds to 150 seconds.

In another embodiment, water is added to the same silica or polypropylene filter and centrifuged at 50 g to 2000 g for 15 seconds to 45 seconds. In yet another embodiment, water is added to the same silica or polypropylene filter and centrifuged at 1,500 g to 2,000 g for 15 seconds to 45 seconds. In yet another embodiment, water is DNase/RNase-free water.

Digesting the biological specimen proceeds to the step of cleaning the biological specimen by interacting the biological specimen with one of at least Proteinase K, Guanidinium thiocyanate, N-Lauroylsarcosine, ethanol, 2-amino-2-(hydroxymethyl) propane-1,3-dihydrochloride, and edetate disodium. In one embodiment, 4 U to 12 U Proteinase K is added to the washed biological specimen and held at 45° C. to 65° C. for 15 minutes to 60 minutes. In one embodiment, 4 U to 8 U Proteinase K is added to the washed biological specimen and held at 45° C. to 65° C. for 15 minutes to 60 minutes. In yet another embodiment, 4 U to 8 U Proteinase K is added to the washed biological specimen and held at 50° C. to 60° C. for 15 minutes to 60 minutes. In yet another embodiment, 4 U to 8 U Proteinase K is added to the washed biological specimen and held at 50° C. to 60° C. for 20 minutes to 40 minutes. In another embodiment, for solid tissue or complex matrices, incubation proceeds for 1 to 3 hours. In another embodiment, 1 to 3 volumes of a mixture of 55% to 85% Guanidinium thiocyanate and 1% to 20% N-Lauroylsarcosine is added to the held biological specimen. In a preferred embodiment, 1 to 2 volumes of 55% to 85% Guanidinium thiocyanate and 1% to 20% N-Lauroylsarcosine is added to the held biological specimen. In yet another preferred embodiment, 1 to 2 volumes of 65% to 75% Guanidinium thiocyanate and 1% to 10% N-Lauroylsarcosine is added to the held biological specimen.

In one embodiment, a buffer solution of 55% to 85% Guanidinium thiocyanate and 1% to 20% N-Lauroylsarcosine is mixed in equal volumes with a solution of 70% to 100% ethanol. In one embodiment, a buffer solution of 65% to 75% Guanidinium thiocyanate and 1% to 10% N-Lauroylsarcosine is mixed in equal volumes with a solution of 70% to 100% ethanol. In still another embodiment, a buffer solution of 65% to 75% Guanidinium thiocyanate and 1% to 10% N-Lauroylsarcosine is mixed in equal volumes with a solution of 90% to 100% ethanol. In the embodiments, the biological specimen is now cleaned and ready to digest and isolate a test sample from the biological specimen.

Digesting the biological specimen proceeds to the step of isolating a test sample from the biological specimen by interacting the biological specimen with one of at least 55% to 85% Guanidinium thiocyanate, 1% to 20% N-Lauroylsarcosine, 70% to 100% ethanol, DNase I, 2-amino-2-(hydroxymethyl)-propane-1,3-dihydrochloride, and edetate disodium. In one embodiment, the biological specimen is first centrifuged at >10,000 g for 1 minute. In another embodiment, the supernatant of the centrifuged biological specimen is transferred to a new silica or polypropylene filter and centrifuged at >10,000 g for 1 minute. The material that passes through the filter is the biological specimen and is retained.

In another embodiment, 1 to 3 volumes of 70% to 100% ethanol are added to the biological specimen in a mixture of 25% to 85% Guanidinium thiocyanate and 1% to 20% N-Lauroylsarcosine; the resulting solution is mixed well, either through manual inversion or vortexing, or other methods known in the art. In a preferred embodiment, 1 to 2 volumes of 90% to 100% ethanol are added to the clinical specimen in a mixture of 65% to 76% Guanidinium thiocyanate and 1% to 10% N-Lauroylsarcosine, and the resulting solution is mixed well.

In another embodiment, the resulting solution is transferred to a silica or polypropylene filter and centrifuged at 10,000 g to 16,000 g for 15 to 60 seconds. In a preferred embodiment, the resulting solution is centrifuged for 15 seconds to 45 seconds. The material that passes through the filter is discarded.

In another embodiment, 200 μL to 600 μL of a mixture of 25% to 85% Guanidinium thiocyanate and 1% to 20% N-Lauroylsarcosine is added to the silica or polypropylene filter, and the filter is centrifuged for at 10,000 g to 16,000 g for 15 to 60 seconds. In a preferred embodiment, 65% to 75% Guanidinium thiocyanate and 1% to 10% N-Lauroylsarcosine is added to the silica or polypropylene filter, and the filter is centrifuged for at 10,000 g to 16,000 g for 15 to 45 seconds. The material that passes through the filter is discarded.

In another embodiment, 1 U to 15 U DNaseI is added to the silica or polypropylene filter and is held at room temperature for 10 minutes to 25 minutes. In a preferred embodiment, 3 U to 8 U DNaseI is added to the silica or polypropylene filter and is held at room temperature for 10 minutes to 25 minutes. In yet another preferred embodiment, 3 U to 8 U DNaseI is added to the silica or polypropylene filter and is held at room temperature for 12 minutes to 20 minutes. In another embodiment, 200 μL to 700 μL of a mixture of 25% to 55% Guanidinium chloride and 70% to 99% ethanol is added to the silica or polypropylene filter and centrifuged at 10,000 g to 16,000 g for 15 to 60 seconds. In a preferred embodiment, 300 μL to 500 μL of a mixture of 35% to 45% Guanidinium chloride and 95% to 99% ethanol is added to the silica or polypropylene filter and centrifuged at 10,000 g to 16,000 g for 15 to 45 seconds. In another embodiment, 400 μL to 900 μL of a mixture of 12 mg/m$^3$ to 790 mg/m$^3$ 2-amino-2-(hydroxymethyl) propane-1,3-dihydrochloride, and 20 mg/m$^3$ to 2,000 mg/m$^3$ edetate disodium is added to the silica or polypropylene filter and centrifuged at 10,000 g to 16,000 g for 15 to 60 seconds. In one embodiment, 600 μL to 800 μL of a mixture of 25 mg/m$^3$ to 600 mg/m$^3$ 2-amino-2-(hydroxymethyl) propane-1,3-dihydrochloride, and 50 mg/m$^3$ to 1,000 mg/m$^3$ edetate disodium is added to the silica or polypropylene filter and centrifuged at 10,000 g to 16,000 g for 15 to 45 seconds. In another embodiment, a second mixture of 200 μL to 700 μL of a mixture of 12 mg/m$^3$ to 790 mg/m$^3$ 2-amino-2-(hydroxymethyl) propane-1,3-dihydrochloride, and 20 mg/m$^3$ to 2,000 mg/m$^3$ edetate disodium is added to the silica or polypropylene filter and centrifuged at 10,000 g to 16,000 g for 60 to 180 seconds. In one embodiment, a second mixture of 300 μL to 500 μL of a mixture of 25 mg/m$^3$ to 600 mg/m$^3$ 2-amino-2-(hydroxymethyl) propane-1,3-dihydrochloride, and 50 mg/m$^3$ to 1,000 mg/m$^3$ edetate disodium is added to the silica or polypropylene filter and centrifuged at 10,000 g to 16,000 g for 90 to 150 seconds. In another embodiment, water is added to the same silica or polypropylene filter and centrifuged at 10,000 g to 16,000 g for 15 seconds to 450 seconds. The material that passes through the filter is the test sample and is retained.

The test sample from the biological specimen may optionally be further completed by boiling, treating with a denaturant, or storing at −70° C. In one embodiment, the test sample may be completed by boiling at 100° C. to 120° C. for 10 minutes to 30 minutes; in another embodiment, the test sample may be completed by boiling at 100° C. to 105° C. for 10 minutes to 20 minutes. In another embodiment, the test sample may be completed by treating the test sample with a denaturant with 25% to 50% of one of at least polysorbate 20; polysorbate 80; (1,1,3,3-Tetramethylbutyl) phenyl-polyethylene glycol, Polyethylene glycol tert-octylphenyl ether; and 4-(1,1,3,3-Tetramethylbutyl)phenyl-polyethylene glycol, t-Octylphenoxypolyethoxyethanol, Polyethylene glycol tert-octylphenyl ether.

In another embodiment, the test sample may be completed by storing at −70° C. The test sample contains large RNA molecules, small RNA molecules, tRNA molecules, rRNA molecules, mRNA molecules, denatured and non-denatured RNA molecules, microbial RNA molecules, non-microbial RNA molecules, and is now ready to undergo the step of using liquid chromatography 300 to isolate and collect microbial RNA molecules from the test sample.

Using liquid chromatography to bulk filter microbial RNA molecules from the test sample proceeds by injecting the test sample into a sample port of a liquid chromatography instrument 310. In one embodiment, injection volumes are 0.1 mL to 2 mL. In one embodiment, injection volumes are 0.5 to 1.5 mL. Within the liquid chromatography instrument 310, the test sample is carried by pumps at a prescribed flow rate over a porous stationary phase column using a liquid mixture referred to as a mobile phase. The process is controlled by a computer 320. The test sample is traditionally processed by the liquid chromatography instrument 310 to separate into components with similar properties, and the component of interest. Typically, all components of the test sample travel through the liquid chromatography instrument 310 to a waste line. However, in various embodiments of the present disclosure, either automatically or manually, regions with components of interest 330 are diverted to a collection container for further identification. In various embodiments, components of interest 330 in the form of microbial RNA are detected using either a diode array, UV-Vis, or a refractive index detector. Regions without components of interest 340 are detected as a flat line ("baseline").

The liquid chromatography instrument filters the microbial RNA molecules from non-microbial RNA molecules to isolate and collect these molecules by decreasing and then increasing the amount of an organic buffer in a mobile phase in relation to an aqueous buffer in said mobile phase. In one embodiment, the amount of organic buffer in the mobile phase varies between 20% and 100%, as shown in Table 2.

TABLE 2

Mobile phase composition for isolation and collection of microbial RNA.

| Time | % Aqueous Buffer | % Organic Buffer |
|---|---|---|
| 0 | 60-80 | 20-40 |
| 1 | 50-70 | 30-50 |
| 16 | 40-60 | 40-60 |
| 22 | 30-50 | 50-70 |
| 22.5 | 20-40 | 60-80 |
| 23 | 0-20 | 80-100 |
| 24 | 0-20 | 80-100 |
| 25 | 60-80 | 20-40 |
| 27 | 60-80 | 20-40 |

In one embodiment, amount of organic buffer in the mobile phase varies between 30% and 100%, as shown in Table 3.

TABLE 3

Mobile phase composition for isolation and collection of microbial RNA.

| Time | % Aqueous Buffer | % Organic Buffer |
|---|---|---|
| 0 | 60-70 | 30-40 |
| 1 | 55-65 | 35-45 |
| 16 | 35-45 | 55-65 |
| 22 | 30-40 | 60-70 |
| 22.5 | 25-35 | 65-75 |
| 23 | 0-10 | 90-100 |
| 24 | 0-10 | 90-100 |
| 25 | 60-70 | 30-40 |
| 27 | 60-70 | 30-40 |

In some aspects, the void volume elutes in the liquid chromatography mobile phase when the percent aqueous buffer is greater than about 40%, in some aspects greater than about 45%, in some aspects greater than about 50%, in some aspects greater than about 55%, and in some aspects greater than about 60%. In some aspects, the void volume elutes in the liquid chromatography mobile phase when the percent organic buffer is less than about 60%, in some aspects less than about 55%, in some aspects less than about 50%, in some aspects less than about 45%, and in some aspects less than about 40%.

In one embodiment, the flow rate of the liquid chromatography mobile phase, as delivered by the pumps is 0.5 mL to 3.5 mL/min. In one embodiment, the flow rate of the liquid chromatography mobile phase, as delivered by the pumps, is 1 mL/min to 2.5 mL/min. In yet another embodiment, the flow rate of the liquid chromatography mobile phase, as delivered by the pumps, is 1 mL/min to 1.5 mL/min.

In some aspects, a flow rate of the mobile phase in the liquid is about 0.5 mL/min. to about 3.5 mL/min., in some aspects about 550 μL/min. to about 2 mL/min., in some aspects about 600 μL/min. to about 1 mL/min., and in some other aspects about 650 μL/min. to about 850 μL/min.

The mobile phase is delivered as a mixture of two buffers, on an organic buffer and the other an aqueous buffer. In one embodiment, the aqueous buffer is comprised of at least one of at least 0.05 to 0.9M triethylammonium acetate, phosphoric acid, citric acid, ammonium bicarbonate, formic acid, lactic acid, 2-[4-(2-hydroxyethyl)piperazin-1-yl]ethanesulfonic acid, maleic acid, diethanolamine, piperidine, ethanolamine, and triethanolamine. In particular, a 0.05M to 0.5M buffer comprised of at least one of triethylammonium acetate, formic acid, lactic acid, 2-[4-(2-hydroxyethyl)piperazin-1-yl]ethanesulfonic acid, maleic acid, triethanolamine, and piperidine is used; more preferably a 0.05 M to 0.2M solution of aqueous buffer of at least one of triethylammonium acetate, formic acid, 2-[4-(2-hydroxyethyl)piperazin-1-yl]ethanesulfonic acid, maleic acid, and triethanolamine, is used.

In another embodiment, the organic buffer is comprised of a mixture of a 0.05 M to 0.9 M aqueous buffer solution in one of at least 5% to 60% acetonitrile, methanol, ethanol, 1-propanol, 2-propanol, acetone, and tetrahydrofuran; in particular, the organic buffer is comprised of a mixture of 0.05 M to 0.5 M aqueous buffer solution in at least one of 7% to 50% acetonitrile, methanol, ethanol, 1-propanol, and acetone. In one embodiment, the organic buffer is comprised of a mixture of 0.05 M to 0.5 M aqueous buffer solution in at least one of 10% to 40% acetonitrile, methanol, and acetone.

In the method according to various embodiments, a nonpolar compound serves as the porous stationary phase column, either in the form of polymeric heads, polymeric microspheres, or a polymerized block. Irrespective of its precise faint, the polymeric stationary phase column is porous in nature, which means that the polymeric stationary phase column is characterized by pores. The stationary phase column material may be commercially available and be uncoated or coated with specialized polymeric compounds designed to cover pores on the bead or microsphere surface to prevent microbial RNA from irreversibly interacting with the stationary phase column material. Within an outer structure of the stationary phase column are polymeric microspheres, preferably comprised of alkylated non-porous polystyrene-divinylbenzene copolymer. The stationary phase column is provided with a microsphere particle size of 8.0 μm to 50 μm, preferably 8.0 μm to 25 μm. The resulting pore size of the stationary phase column is 1000 Å to 5000 Å, in particular a pore size of 1000 Å to 4000 Å, more preferably 2000 Å to 4000 Å, or 2500 to 4000 Å. The stationary phase column may have dimensions of 4 mm to 30 mm wide by 40 mm to 150 mm long, preferably 5 mm to 10 mm wide by 40 mm to 100 mm long, even more preferably 7 mm to 9 mm wide by 40 to 60 mm long.

According to one embodiment, the stationary phase column may be operated at ambient temperature, or more preferably controlled at a temperature of 20° C. to 27° C.

Microbial RNA is filtered and isolated from non-microbial RNA in the stationary phase column through selective interactions with the mobile phase and stationary phase column microspheres and pores. As the filtration and isolation occurs, the microbial and non-microbial RNA exit, or elute, from the stationary phase column at different times, and are detected by a detector, with microbial RNA eluting in the void volume of the column. In one embodiment, detection of the isolated microbial RNA is accomplished with a UV-Vis or diode array detector, coupled to the liquid chromatography instrument at the exit of the stationary phase column, at 200 nm to 220 nm, in particular at 203 nm to 217 nm, and still more preferably at 205 nm to 215 nm. In another embodiment, detection of the isolated microbial RNA is accomplished with a UV-Vis or diode array detector, coupled to the liquid chromatography instrument at the exit of the stationary phase column, at 250 nm to 270 nm, in particular 257 nm to 267 nm, and still more preferably 255 nm to 265 nm. In another embodiment, detection of the isolated microbial RNA is accomplished with a refractive index detector, coupled to the liquid chromatography instrument at the exit of the stationary phase column, set with a refractive index default range of 0.75 RI to 2.00 RI, in particular a default range of 0.9 RI to 1.90 RI, and still more preferably a default range of 1.00 RI to 1.75 RI.

Figure 2:
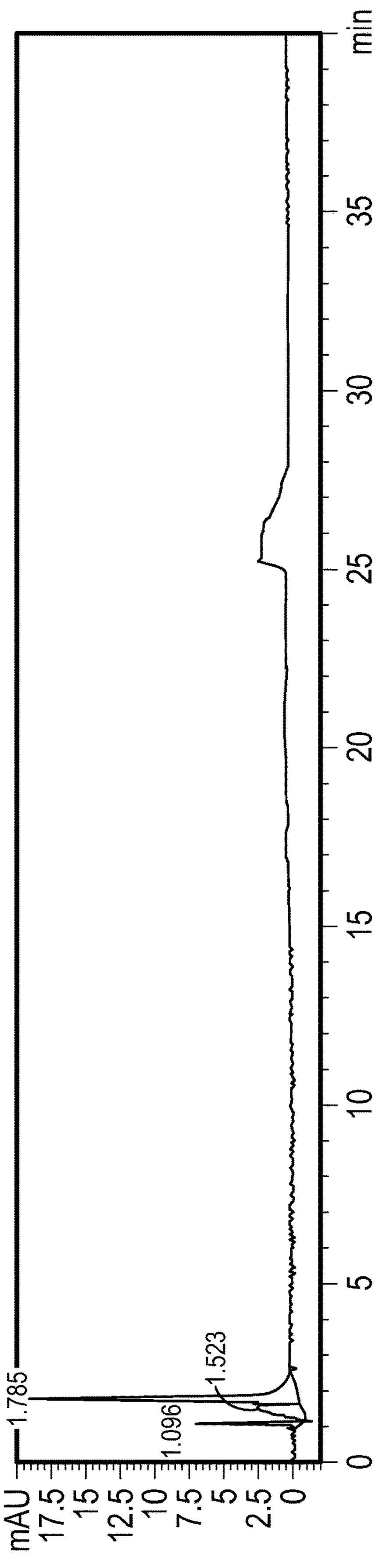
FIG. 2 shows a representative chromatogram of a separation of microbial RNA.
Figure 3:
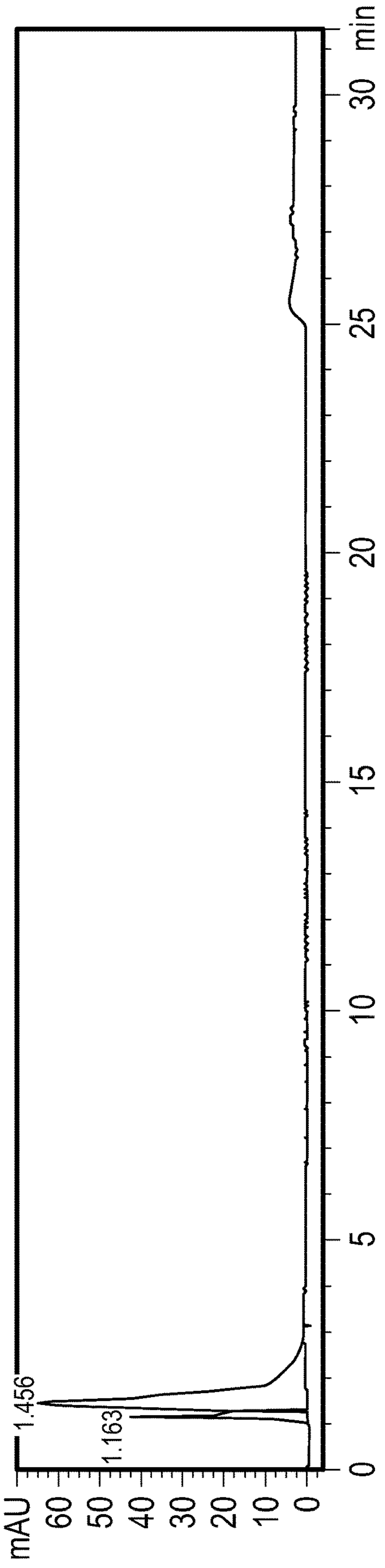
FIG. 3 shows a representative chromatogram of a separation of microbial RNA.

Isolated microbial RNA is detected in a trace of data referred to as a chromatogram. Exemplary chromatograms of isolated microbial RNA are found in FIGS. 2 and 3. The peaks observed in the window of 0 minutes to 3 minutes, correspond to isolated microbial RNA. Non-microbial RNA would be detected in the window of 7 minutes to 15 minutes, as disclosed by Ketterer et al (c.f. U.S. Pat. No. 8,383,340). When the microbial RNA is detected, the mobile phase, containing compounds of interest (e.g. microbial RNA), is diverted from the waste line to a sample collection vial for future identification or experiments.

In some aspects, the sample collection of mobile phase from liquid chromatography includes the void volume and at least a portion of the mobile phase corresponding to the peaks relating to non-microbial RNA. In some aspects, the mobile phase containing compounds of interest (e.g., microbial RNA) may be collected in one or more fractions of eluted sample. In some aspects, a plurality of fractions of eluted sample are collected based upon time, volume, or both, as the mobile phase containing any compounds of interest elute from the column.

In some aspects, each fraction is collected from the column at a period of time between about 5 seconds and about 1 minute, in some aspects between about 10 seconds and about 45 seconds, and in some aspects between about 15 seconds and about 30 seconds. In some aspects, each fraction collected has a volume between about 100 μL to about 1 mL, in some aspects between about 125 μL to about 750 μL, in some aspects between about 150 μL to about 500 μL, and in some aspects between about 175 μL to about 250 μL.

In some aspects, at least a portion of the void volume may be collected in a quantity of desired fractions between at least one 1 fraction and up to about 72 fractions, in some aspects at least 1 fraction up to about 36 fractions, and in some other aspect at least 1 fraction up to about 24 fractions.

After the sample volume is collected from the liquid chromatography in one or more fractions, each of the one or more fractions may be subjected to gene sequencing.

In one embodiment, microbial RNA is detected from one or more fractions eluted from the void volume using liquid chromatography, wherein the microbial RNA is detected from at least one of the one or more fractions eluted from the void volume using gene sequencing.

In some aspects, each fraction is subjected to dehydration prior to gene sequencing, wherein each fraction is dehydrated to a volume between about 15 μL and about 500 μL, in some aspects between about 20 μL and about 100 μL, in some aspects between about 25 μL and about 75 μL, and in some preferred aspects between about 35 μL and about 65 μL.

In some aspects, a control may be introduced into the biological sample to normalize and/or monitor the microbial RNA relative to the non-microbial RNA. In some aspects, the control may be introduced into the biological sample prior to the step of digesting the biological specimen, after the biological specimen is digested, with the test sample that is introduced into the liquid chromatography, or when the desired sample is subjected to gene sequencing. The control is preferably chosen such as to elute from the column within both the void volume and the normal sample separate volume. The control may be chosen from any desired source that does not interfere with the microbial RNA or the sample RNA. In some preferred aspects, the control is a synthetically derived RNA such as an ERCC RNA control, such as ERCC RNA control Ambion™ commercially available from ThermoFisher Scientific.

Using various embodiments in accordance with this disclosure, it is possible to simultaneously isolate and collect all microbial RNA of interest, thereby allowing for future identification of all viable (live) microbial species within a biological specimen, or subsequent structural elucidation, quantitation, or qualitative analysis of the microbial RNA. Various embodiments of the present disclosure allow for simultaneous isolation and collection of microbial RNA from gram positive bacteria, gram negative bacteria, bacterial spores, enveloped viruses, non-enveloped viruses, RNA viruses, fungi, yeast, and protozoa. Exemplary microbial species within the test sample that are filtered, isolated and collected as microbial RNA using the method of the present disclosure, are found in Table 4.

TABLE 4

Microbial species detected by isolating and collecting RNA from clinical specimens.

| Species Detected | Gram (+) | Gram (−) | Virus, Protozoa, Yeast, or Fungi |
|---|---|---|---|
| *E. coli* | | Y | |
| *E. coli* O157 | | Y | |
| *S. aureus* | Y | | |
| *Campylobacter jejuni* | | Y | |
| *S. typhi* | | Y | |
| *C. perfringens* | Y | | |
| *C. botulinum* | Y | | |
| *B. burgdorferi* | | Y | |
| Norovirus | | | Y |
| *B. mayonii* | | Y | |
| *C. parvum* | | | Y |
| *L. monocytogenes* | Y | | |
| *S. sonnei* | | | |
| *L. pneumophila* | | Y | |
| *P. aeruginosa* | | Y | |
| *C. albicans* | | | Y |
| *M. tuberculosis* | Y | | |

Figure 4:
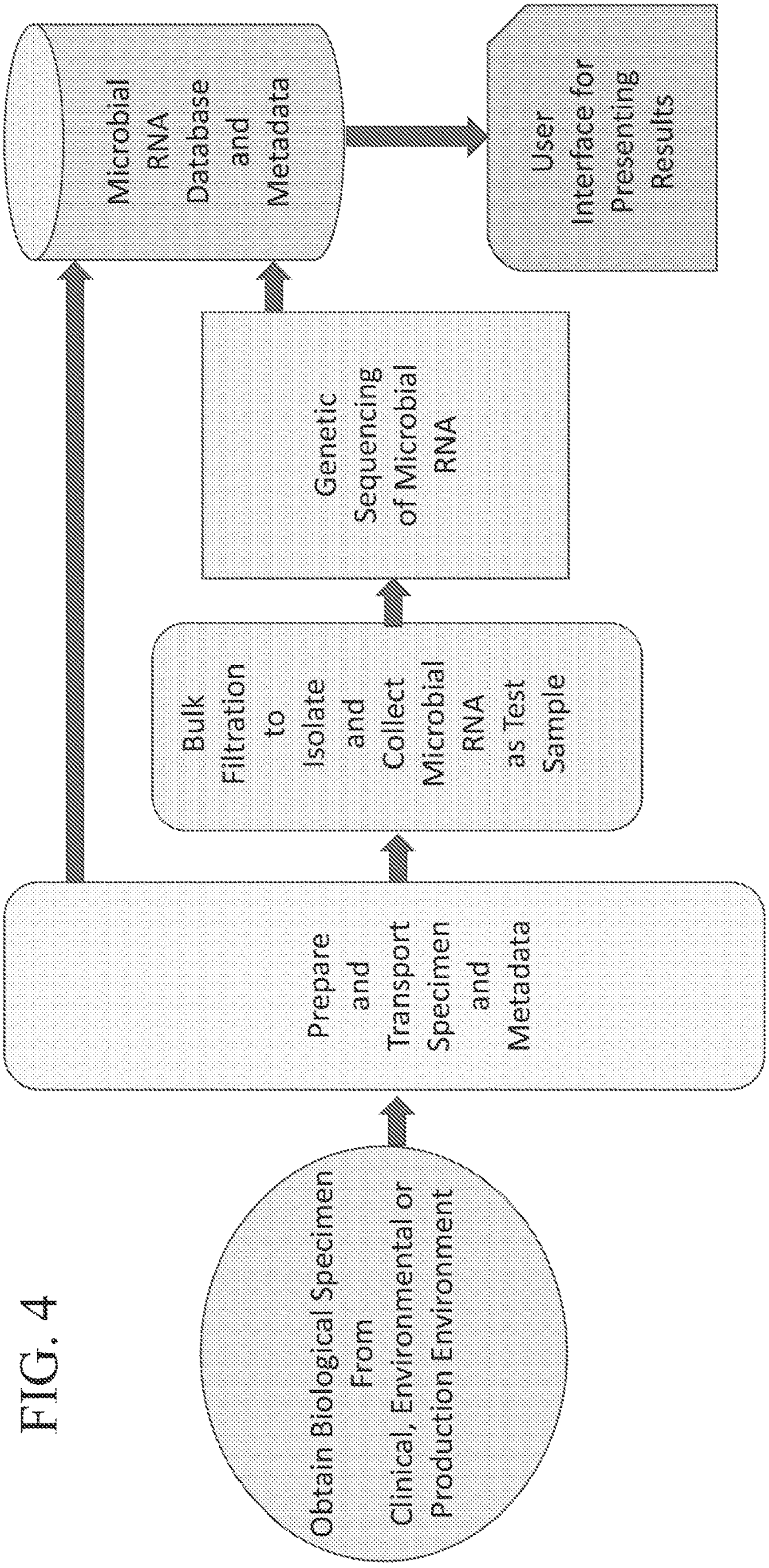
FIG. 4 shows a representative block diagram of one embodiment of an overall workflow incorporating the bulk filtration method as part of an overall process for identifying microbial RNA in a biological specimen.

FIG. 4 shows a representative block diagram of one embodiment of an overall workflow incorporating the bulk filtration method as part of an overall process for identifying microbial RNA in a biological specimen. At 410, a biological specimen 402 is sampled and collected from either a clinical, production or environmental context. Although the biological specimen may be processed in accordance with various embodiments which equipment located proximate the context where it was sampled, in other embodiments, the biological specimen 402 is transported at 420 to a different facility to perform the filtration method in accordance with various embodiments. Through the various embodiments, the biological specimen is transformed into a test sample to allow for isolation and collection of microbial RNA using liquid chromatography. At 430, a test sample 404 containing the isolated and collected microbial RNA is produced in a void volume of an HPLC, in accordance with the various embodiments. The test sample 404 with only the microbial RNA is then sequenced at 440 to identify all viable (live) microbial species within the test sample. In other embodiments, 440 can include structural elucidation, quantitation, or qualitative analysis of the microbial RNA. The results of the identification of viable microbial species from the biological specimen can be collected in a database 450 and presented or reported out via a user interface 460, accessible via a secure network interface.

EXAMPLE

A test was conducted to using liquid chromatography to filter a mixture of microbial RNA and human RNA with subsequent library preparation for gene sequencing. The materials used included Universal Human Reference (Thermofisher QS0639; Lot 244273) as the human RNA, *E. coli* Total RNA (Thermofisher AM7940; Lot 2219538) as the microbial RNA, RoboSep column, Wave Optimized® A, Wave Optimized® B, Wave Optimized® C, and Ultrapure Nuclease Free Water (NFW).

The HPLC (Agilent 1260 Infinity II) was set up for a constant flow rate of 0.75 mL/min., the column was held at a temperature of about 75° C. for the entire course of the run, DAD was set to detect at 260 nm (bandwidth of 1 nm), the fraction collector was set to collect 15 second fractions between 0:30 and 12 minutes, and there was a 50 μL injection of sample. The HPLC was set to have a mobile phase gradient shown in Table 5.

TABLE 5

Mobile Phase Elution Gradient (flow rate 0.75 mL/min.).

| Time | % Buffer A | % Buffer B |
|---|---|---|
| 0 | 62 | 38 |
| 1 | 60 | 40 |
| 16 | 40 | 60 |
| 22 | 34 | 66 |
| 22:30 | 30 | 70 |
| 23 | 0 | 100 |
| 25 | 62 | 38 |

Human RNA was diluted with Ultrapure Nuclease Free Water from 1,000 ng/μL to 50 ng/μL by diluting the whole 10 μL stock with 190 μL of chilled NFW. *E. coli* RNA was diluted with NFW to 10 ng/μL in two steps: (i) 10 μL of Stock 1,000 ng/μL *E. coli* RNA was diluted into 90 μL of chilled NFW—resulting in a 100 ng/μL aliquot, and (ii) 10 μL of the 100 ng/μL dilution level was diluted into 90 μL of chilled NFW—resulting in a 10 ng/μL aliquot. 19 μL of the 50 ng/μL Human RNA (950 ng) was mixed with 5 μL of 10 ng/μL *E. coli* RNA (50 ng) to create a sample with 5% *E. coli*

RNA relative to human RNA. The mixture was brought to 100 μL with 76 μL of chilled NFW.

Figure 5A:
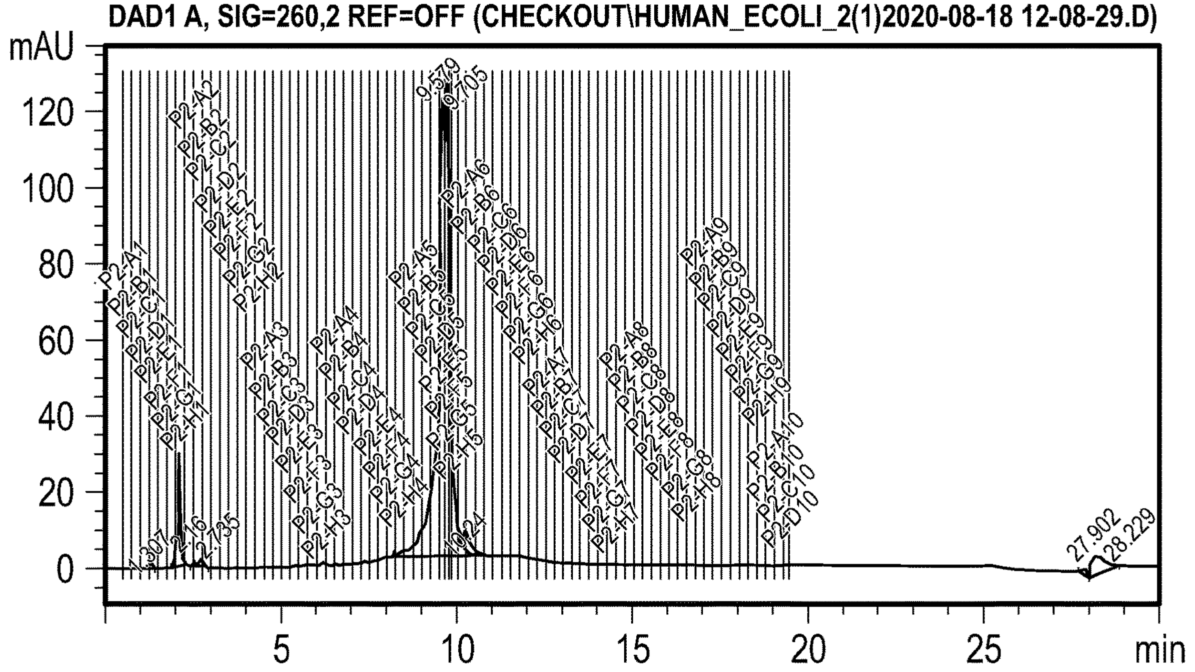
FIG. 5A shows a representative chromatogram of a separation of a sample having *E. coli* RNA combined into *Homo sapiens* RNA with fractions collected every 15 seconds and retention times overlayed the 15-second fractions, which illustrate peaks within each fraction, including the void volume, in accordance with certain embodiments of the present invention.
Figure 5B:
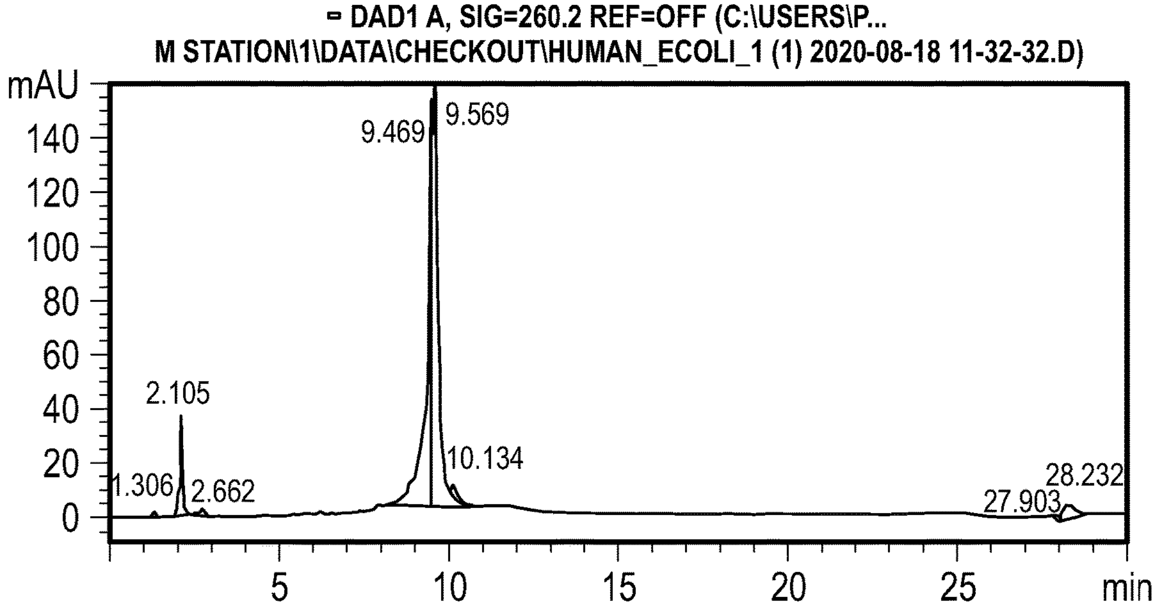
FIG. 5B is the chromatogram of FIG. 5A without the retention time overlayed each of the 15-second fractions.

The mixed RNA sample was then filtered on the HPLC with fraction collection by plating the mixture sample into position A1 of a new sterile PCR plate and loaded into the HPLC holding at 4° C. The method was started and 50 μL of sample (~500 ng) was injected onto the column. Fractions between 0:30 and 12 minutes were collected in a new sterile PCR plate at 15-second intervals (i.e. 2 fractions per 30-second collection). Each collected fraction was about 0.188 mL every 15 seconds. This time aligns with sizes between ~0-6000 nt based on RiboRubler High Range Ladder runs with this protocol. The chromatograph in FIGS. 444. 5A-5B was obtained for the sample. As illustrated in the chromatograph in FIGS. 5A-5B of every 15-second fraction, minor peaks eluted from the column in the void volume at approximately retention times of 1.3, 2.1, and 2.7 minutes, while major peaks eluted from the column after 8 minutes up to about 12 minutes.

The peaks between 0:30 and 6 minutes had low absorbance of RN. Without wishing to be bound by theory, it is believed to that these fractions in the void volume were likely composed of small RNA molecules, fractions of RNA, RNA molecules having secondary and tertiary features, and/or mRNAs. After the void volume (e.g., in the 8 to 12 minute retention time) there are two large peaks, which without wishing to be bound by theory, that are likely composed of larger mRNA transcripts or rRNA transcripts.

Figure 6A:
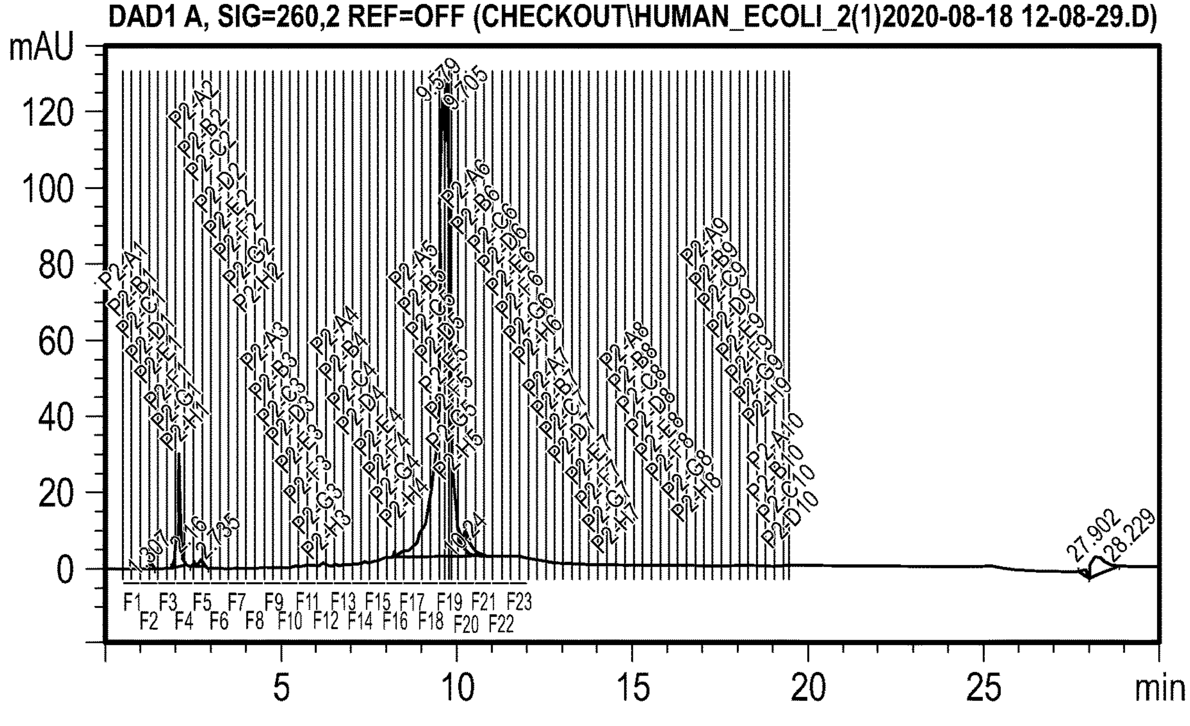
FIG. 6A shows another representative chromatogram of the separation of a sample having *E. coli* RNA combined into *Homo sapiens* RNA being reproducible, such that the fractions collected every 15 seconds have very similar peaks within each fraction, including the void volume, in accordance with certain embodiments of the present invention.
Figure 6B:
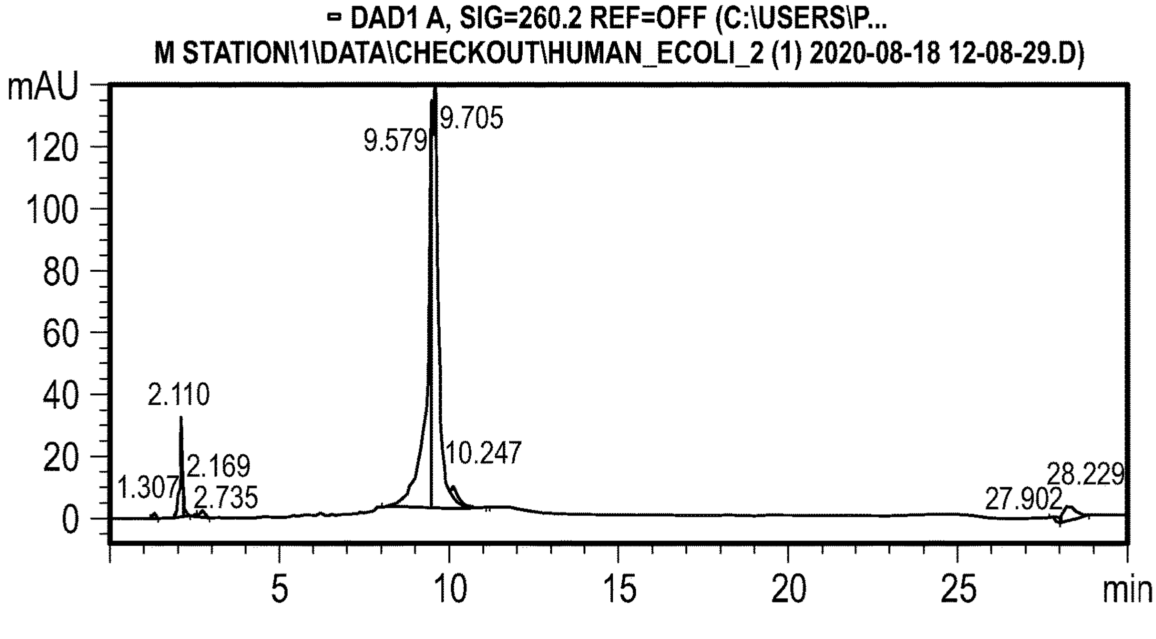
FIG. 6B is the chromatogram of FIG. 6A without the retention time overlayed each of the 15-second fractions.

The method was repeated with another 50 μL of sample (~500 ng) injected onto the column. The chromatograph in FIG. 6 was obtained for the repeated sample. The chromatographs in FIGS. 5 and 6 are virtually identical confirming the repeatability of the method.

The collected fractions were then concentrated prior to RNA quantification with the Zymo Clean and Concentrate-5 kit. Two of the 15-second collected fractions for times between 0:30 and 12 minutes were combined (e.g., 0:30-0:45 and 0:45-1 minute, 1-1:15 and 1:15-1:30, etc.) into a sterile, nuclease-free 5 mL tube, to provide about 375 μL of combined fraction. 750 μL (2× fraction volume) of RNA binding buffer was added to each fraction and then mixed well by shaking. 1.125 μL of 200 Proof Ethanol (IX Fraction+Buffer volume) was added to the mixture and then was mixed well by shaking. Up to 800 μL of the mixture was then applied to a silica filter and spun to bind at 10,000×g for 30 seconds, which took 3 steps. 400 μL of RNA Prep Buffer was applied to the filter following binding of all RNA, which was then washed at 10,000×g for 30 seconds. 700 μL of RNA Wash Buffer was then applied to the filter after removal of previous flow through and was washed at 10,000×g for seconds. Flow through was dumped and then 400 μL of RNA Wash Buffer was applied to the filter and was washed at 10,000×g for 1 minute. The column was then carefully transferred to a fresh, sterile, nuclease-free microcentrifuge tube. Once in a fresh, identically labeled tube 15 μL of nuclease-free water was applied to the filter and all RNA was eluted at 10,000×g for 1 minute.

The fraction concentration corresponding to the resulting fraction for gene sequencing is provided in Table 6.

TABLE 6

Fraction Table between HPLC Fraction and Assay Fraction.

| HPLC Fraction | Assay Fraction | Time Start | Time End |
|---|---|---|---|
| Fraction 1 | Fraction 1 | 0:30 | 1:00 |
| Fraction 2 | | | |
| Fraction 3 | Fraction 2 | 1:00 | 1:30 |
| Fraction 4 | | | |
| Fraction 5 | Fraction 3 | 1:30 | 2:00 |
| Fraction 6 | | | |
| Fraction 7 | Fraction 4 | 2:00 | 2:30 |
| Fraction 8 | | | |
| Fraction 9 | Fraction 5 | 2:30 | 3:00 |
| Fraction 10 | | | |
| Fraction 11 | Fraction 6 | 3:00 | 3:30 |
| Fraction 12 | | | |
| Fraction 13 | Fraction 7 | 3:30 | 4:00 |
| Fraction 14 | | | |
| Fraction 15 | Fraction 8 | 4:00 | 4:30 |
| Fraction 16 | | | |
| Fraction 17 | Fraction 9 | 4:30 | 5:00 |
| Fraction 18 | | | |
| Fraction 19 | Fraction 10 | 5:00 | 5:30 |
| Fraction 20 | | | |
| Fraction 21 | Fraction 11 | 5:30 | 6:00 |
| Fraction 22 | | | |
| Fraction 23 | Fraction 12 | 6:00 | 6:30 |
| Fraction 24 | | | |
| Fraction 25 | Fraction 13 | 6:30 | 7:00 |
| Fraction 26 | | | |
| Fraction 27 | Fraction 14 | 7:00 | 7:30 |
| Fraction 28 | | | |
| Fraction 29 | Fraction 15 | 7:30 | 8:00 |
| Fraction 30 | | | |
| Fraction 31 | Fraction 16 | 8:00 | 8:30 |
| Fraction 32 | | | |
| Fraction 33 | Fraction 17 | 8:30 | 9:00 |
| Fraction 34 | | | |
| Fraction 35 | Fraction 18 | 9:00 | 9:30 |
| Fraction 36 | | | |
| Fraction 37 | Fraction 19 | 9:30 | 10:00 |
| Fraction 38 | | | |
| Fraction 39 | Fraction 20 | 10:00 | 10:30 |
| Fraction 40 | | | |
| Fraction 41 | Fraction 21 | 10:30 | 11:00 |
| Fraction 42 | | | |
| Fraction 43 | Fraction 22 | 11:00 | 11:30 |
| Fraction 44 | | | |
| Fraction 45 | Fraction 23 | 11:30 | 12:00 |
| Fraction 46 | | | |

The eluted RNA fraction was then quantified using Quanti-T RNA HS assay set up with 6,766 μL of Quant-iT RNA Buffer added to a 15 mL conical tube and 34 μL of Quant-iT RNA Reagent then added to the buffer and mixed by vortexing for 10 seconds. A 3 μL aliquot of each Assay Fraction in Table 6 was plated (3 μL RNA input) with standards in column 12. The plate was then read on a Tecan infinite pro 200 plate reader following 30 seconds of orbital shaking and 2 minutes of incubation. The quantification results are provided in Table 7.

TABLE 7

RNA Quantification Results.

| Assay Fraction | Reader Results | Background Normalized RFU | Mass of RNA (ng) | Concentration of RNA (ng/μL; 3 μL input) |
|---|---|---|---|---|
| Fraction 1 | 3059 | 1777 | 9.1 | 3.0 |
| Fraction 2 | 1565 | 283 | 1.5 | 0.5 |
| Fraction 3 | 1372 | 90 | 0.5 | 0.2 |
| Fraction 4 | 3629 | 2347 | 12.0 | 4.0 |
| Fraction 5 | 934 | −348 | 0.0 | 0.0 |
| Fraction 6 | 1382 | 100 | 0.5 | 0.2 |

TABLE 7-continued

| RNA Quantification Results. | | | | |
|---|---|---|---|---|
| Assay Fraction | Reader Results | Background Normalized RFU | Mass of RNA (ng) | Concentration of RNA (ng/μL; 3 μL input) |
| Fraction 7 | 1319 | 37 | 0.2 | 0.1 |
| Fraction 8 | 1381 | 99 | 0.5 | 0.2 |
| Fraction 9 | 1333 | 51 | 0.3 | 0.1 |
| Fraction 10 | 1452 | 170 | 0.9 | 0.3 |
| Fraction 11 | 1486 | 204 | 1.0 | 0.3 |
| Fraction 12 | 1544 | 262 | 1.3 | 0.4 |
| Fraction 13 | 1595 | 313 | 1.6 | 0.5 |
| Fraction 14 | 1723 | 441 | 2.3 | 0.8 |
| Fraction 15 | 2138 | 856 | 4.4 | 1.5 |
| Fraction 16 | 2396 | 1114 | 5.7 | 1.9 |
| Fraction 17 | 3987 | 2705 | 13.9 | 4.6 |
| Fraction 18 | 15289 | 14007 | 71.8 | 23.9 |
| Fraction 19 | 41688 | 40406 | 207.2 | 69.1 |
| Fraction 20 | 6678 | 5396 | 27.7 | 9.2 |
| Fraction 21 | 2821 | 1539 | 7.9 | 2.6 |
| Fraction 22 | 3006 | 1724 | 8.8 | 2.9 |
| Fraction 23 | 1648 | 366 | 1.9 | 0.6 |

As provided in Table 7, concentrations of the fractions were between 0.1-69.1 ng/L. These concentrations were used as input to a library preparation to prepare the RNA for sequencing. 7 μL of Purified RNA with 1 μL (15 pg) of synthetic ERCC internal control spike, was input to the NEBBEXT Single Cell/Low Input RNA Library preparation protocol for Illumina with NEBNext Multiplex Oligos for Illumina (96 Unique Dual Index Primer Pairs, which protocol included in summary: (i) 7 μL of the original 5% *E. coli* RNA was prepared in a position for later comparison, (ii) a no-template control (NTC) was added in a position with 3.5 μL of pre-run HPLC flow through and 3.5 μL of NFW from the Zymo Concentrator kit, (iii) fractions 18 and 19 had 1 μL of RNA input each and were brought to 7 μL with NFW, as their concentrations were much higher than the other fractions, and (iv) these two fractions 18 and 19 align with the large peaks in the chromatogram. RT Primers were annealed to RNA after adding 1 μL of Primer to each RNA sample. The Primed RNA was then reverse-transcribed into cDNA using 15 cycles of cDNA amplification and 6 cycles of library PCR. Amplified cDNA was then purified with Ampure XP beads twice to improve purity. Purified cDNA was then quantified using Quant-iT dsDNA 1× assay and had concentrations as provided in Table 8.

TABLE 8

| Concentrations of amplified cDNA. | | |
|---|---|---|
| Assay Fraction | Concentration of cDNA (ng/μL; 3 μL input) | Normalized Concentration (ng/μL) |
| Fraction 1 | 0.8 | 3.2 |
| Fraction 2 | 9.1 | 5.1 |
| Fraction 3 | 11.3 | 5.7 |
| Fraction 4 | 9.2 | 4.7 |
| Fraction 5 | 7.9 | 5.0 |
| Fraction 6 | 12.4 | 4.7 |
| Fraction 7 | 8.5 | 1.1 |
| Fraction 8 | 11.1 | 5.0 |
| Fraction 9 | 9.2 | 5.6 |
| Fraction 10 | 9.9 | 3.7 |
| Fraction 11 | 10.3 | 3.9 |
| Fraction 12 | 10.2 | 5.7 |
| Fraction 13 | 12.3 | 5.2 |
| Fraction 14 | 14.5 | 5.4 |
| Fraction 15 | 0.2 | 0.7 |

TABLE 8-continued

| Concentrations of amplified cDNA. | | |
|---|---|---|
| Assay Fraction | Concentration of cDNA (ng/μL; 3 μL input) | Normalized Concentration (ng/μL) |
| Fraction 16 | 38.5 | 8.7 |
| Fraction 17 | 52.4 | 7.2 |
| Fraction 18 | 56.2 | 6.0 |
| Fraction 19 | 57.4 | 8.1 |
| Fraction 20 | 55.0 | 7.0 |
| Fraction 21 | 57.2 | 8.0 |
| Fraction 22 | 42.5 | 2.4 |
| Fraction 23 | 0.0 | 2.4 |
| NTC | 4.1 | 5.1 |
| 5% *E. coli* | 56.4 | 8.9 |

After quantification, cDNA was normalized to 40 ng input for each sample (except for Fraction 1, Fraction 15 and Fraction 23 which had concentrations unable to input this amount, so the full volume was added per manufacturer protocol). Normalized cDNA was then fragmented and end-repaired. The end-repaired cDNA was then ligated with Illumina adapters. Ligated cDNA was then cleaned up with Ampure XP beads to remove non-ligated adapters. Once purified, the cDNA was then PCR enriched with 6 cycles of library PCR for 20-100 ng cDNA inputs. Following PCR the amplified libraries were purified with Ampure XP beads and were then quantified using Quant-iT dsDNA IX assay with the normalized concentrations provided in Table 8.

Each sample was pooled with 25 ng for each sample (except Fraction 23 which did not have enough input, so the full volume was added). The pooled sample underwent an additional purification using 0.9× volume of Ampure XP beads to remove any residual impurities and to concentrate the sample. The pure pooled sample had a concentration of 9.88 ng/uL (~50 nM at 300 bp expected size). This purified sequencing library was then diluted and denatured following Immunia protocols to loading concentration and was sequenced on a NextSeq 550 with 150 cycle V2 high output chemistry using the indices provided in Table 9.

TABLE 9

| Indicies of Sequences. | | | | |
|---|---|---|---|---|
| Assay Fraction | Index 1 Sequence | Index 1 Sequence | Index 2 | Index2 |
| Fraction 1 | S762 | TTACCGAC | S512 | CGAATACG |
| Fraction 2 | S713 | TCGTCTGA | S586 | GTCCTTGA |
| Fraction 3 | S736 | TTCCAGGT | S543 | CAGTGCTT |
| Fraction 4 | S709 | TACGGTCT | S575 | TCCATTGC |
| Fraction 5 | S732 | AAGACCGT | S550 | GTCGATTG |
| Fraction 6 | S774 | CAGGTTCA | S506 | ATAACGCC |
| Fraction 7 | S747 | TAGGAGCT | S524 | GCCTTAAC |
| Fraction 8 | S794 | TACTCCAG | S590 | GGTATAGG |
| Fraction 9 | S729 | AGTGACCT | S591 | TCTAGGAG |
| Fraction 10 | S777 | AGCCTATC | S526 | TGCGTAAC |
| Fraction 11 | S772 | TCATCTCC | S567 | CTTGCTAG |
| Fraction 12 | S725 | CCAGTATC | S538 | AGCGAGAT |

TABLE 9-continued

| | | | | |
|---|---|---|---|---|
| Fraction 13 | S755 | TTGCGAGA | S566 | TATGGCAC |
| Fraction 14 | S760 | GAACGAAG | S511 | GAATCACC |
| Fraction 15 | S716 | CGAATTGC | S559 | GTAAGGTG |
| Fraction 16 | S708 | GGAAGAGA | S521 | CGAGAGAA |
| Fraction 17 | S702 | TCGGATTC | S523 | CGCAACTA |
| Fraction 18 | S796 | CTGTACCA | S507 | CACAGACT |
| Fraction 19 | S757 | GAGAGTAC | S545 | TGGAAGCA |
| Fraction 20 | S783 | TCTACGCA | S546 | CAATAGCC |
| Fraction 21 | S722 | GCAATTCC | S578 | CTCGAACA |
| Fraction 22 | S710 | CTCAGAAG | S581 | GGCAAGTT |
| Fraction 23 | S770 | GTCCTAAG | S540 | AGCTACCA |
| NTC | S734 | GCGTTAGA | S592 | CAGCATAC |
| *5% E. coil* | S763 | CAAGGTAC | S505 | CGTATCTC |

Single-end FASTQ files were created for each individual HPLC-fraction as well as the original sample prior to HPLC fractionation. All FASTQ files were then subject to processing by conducting quality filtration and sequence annotation of FASTQ files in parallel. Filtered reads were annotated using a manually curated database. All database sequences are filtered of any contaminant reads using a platform, which queries reference genomic nucleic acid sequences for common contaminant reads and masks such regions to prevent systematic mis-annotation. Upon completion, a data-frame consisting of microbial, *Homo sapiens*, and ERCC internal control annotation counts was collated as provided in Table 10.

TABLE 10

Sequence Number Read Counts.

| Sample | Raw Sequences | Filtered Sequences | *Homo sapien* | Microbial Sequences | ERCC Sequences | Unclassified Sequences |
|---|---|---|---|---|---|---|
| Fraction 1 | 19,443,995 | 16,021,728 | 7,635 | 167 | 15,761,774 | 252,152 |
| Fraction 2 | 19,945,431 | 16,345,908 | 2,610 | 128 | 16,015,672 | 327,498 |
| Fraction 3 | 22,173,768 | 18,428,397 | 1,708 | 136 | 18,267,990 | 158,563 |
| Fraction 4 | 20,521,509 | 17,019,763 | 46,036 | 456 | 16,816,281 | 156,990 |
| Fraction 5 | 20,473,302 | 17,004,254 | 75,686 | 340 | 16,768,247 | 159,981 |
| Fraction 6 | 21,168,512 | 17,487,609 | 43,114 | 377 | 17,284,711 | 159,407 |
| Fraction 7 | 13,993,795 | 11,437,449 | 27,155 | 198 | 11,258,111 | 151,985 |
| Fraction 8 | 19,610,735 | 16,079,194 | 42,880 | 1,530 | 15,889,679 | 145,105 |
| Fraction 9 | 22,782,276 | 18,727,182 | 173,424 | 842 | 18,261,311 | 291,605 |
| Fraction 10 | 23,505,345 | 19,405,751 | 385,459 | 1,760 | 18,645,789 | 372,743 |
| Fraction 11 | 20,277,581 | 16,164,116 | 1,239,320 | 2,856 | 14,569,994 | 351,946 |
| Fraction 12 | 20,222,441 | 16,184,334 | 2,003,803 | 2,714 | 13,673,728 | 504,089 |
| Fraction 13 | 20,609,242 | 16,568,932 | 3,516,977 | 4,792 | 12,192,242 | 854,921 |
| Fraction 14 | 21,665,413 | 17,081,271 | 7,478,244 | 17,713 | 8,037,566 | 1,547,748 |
| Fraction 15 | 11,834,067 | 8,899,151 | 5,154,454 | 2,203 | 2,663,934 | 1,078,560 |
| Fraction 16 | 20,172,937 | 16,135,394 | 10,986,964 | 7,148 | 2,975,175 | 2,166,107 |
| Fraction 17 | 23,798,132 | 18,888,828 | 14,612,030 | 7,001 | 1,822,766 | 2,447,031 |
| Fraction 18 | 25,614,923 | 21,040,589 | 17,153,313 | 6,571 | 925,774 | 2,954,931 |
| Fraction 19 | 23,804,231 | 19,934,447 | 15,816,177 | 6,114 | 1,074,930 | 3,037,226 |
| Fraction 20 | 24,799,564 | 20,720,099 | 17,917,547 | 49,549 | 964,025 | 1,788,978 |
| Fraction 21 | 19,852,061 | 16,618,867 | 13,610,476 | 14,239 | 825,973 | 2,168,179 |
| Fraction 22 | 21,492,830 | 18,404,649 | 14,739,431 | 2,625 | 1,537,337 | 2,125,256 |
| Fraction 23 | 69,497 | 43,969 | 32,990 | 138 | 5,457 | 5,384 |
| Original Sample | 17,707,111 | 14,758,794 | 12,894,584 | 3,953 | 226,110 | 1,634,147 |

Figure 7:
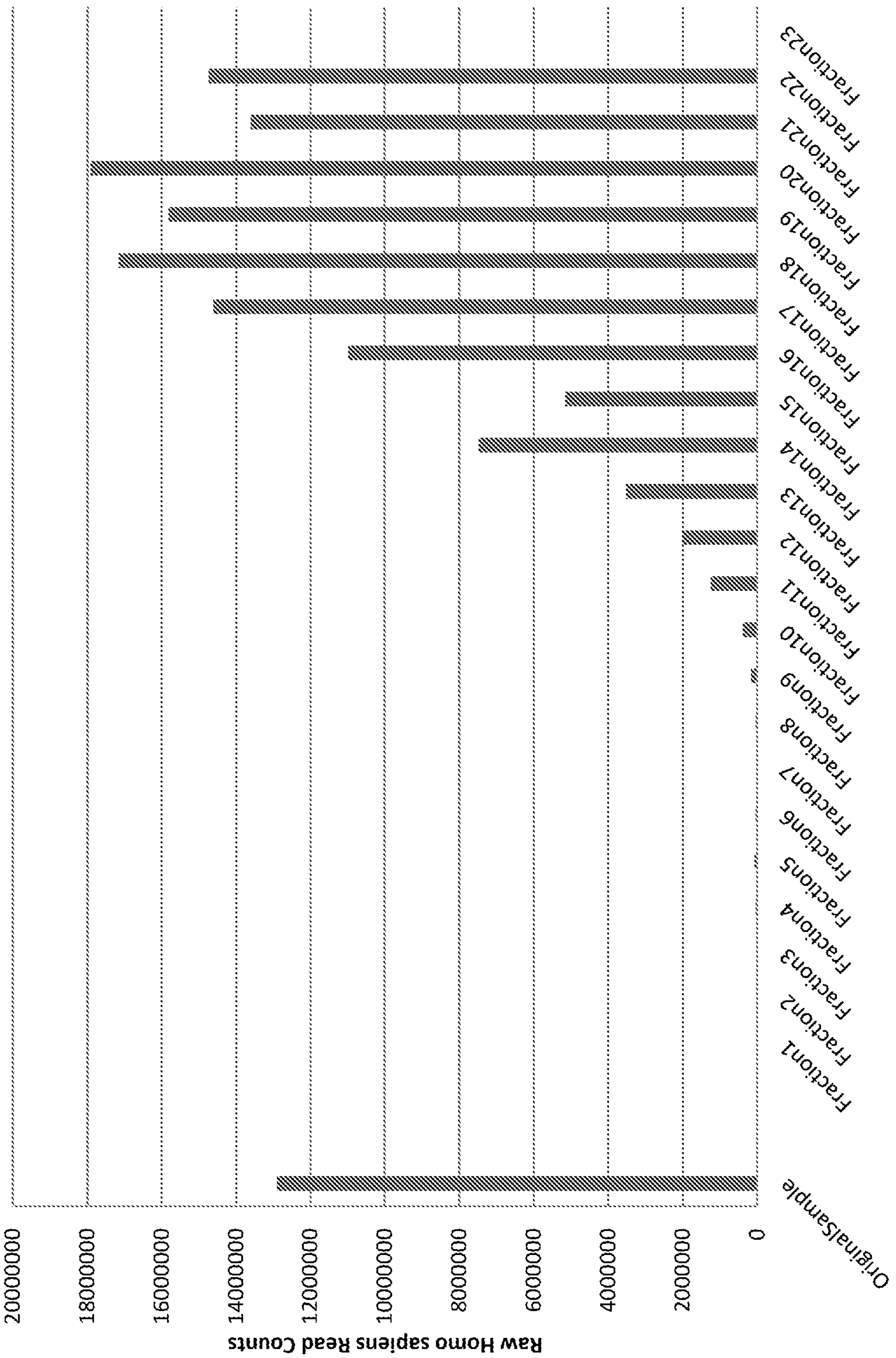
FIG. 7 is a bar graph diagram of raw *Homo sapiens* read counts on the original sample and the sample filtered into fractions 1-23 using liquid chromatography and then gene sequenced, in accordance with certain embodiments of the present invention.

The raw *Homo sapiens* read counts of the original sample and fractions 1-23 are illustrated in the bar graph provided in FIG. 7, which illustrates relatively minimal *Homo sapiens* read counts below Fraction 11. The relative absence of *Homo sapiens* read counts below fraction 11 enhances the microbial RNA presence in these fractions corresponding to the void volume.

Figure 8:
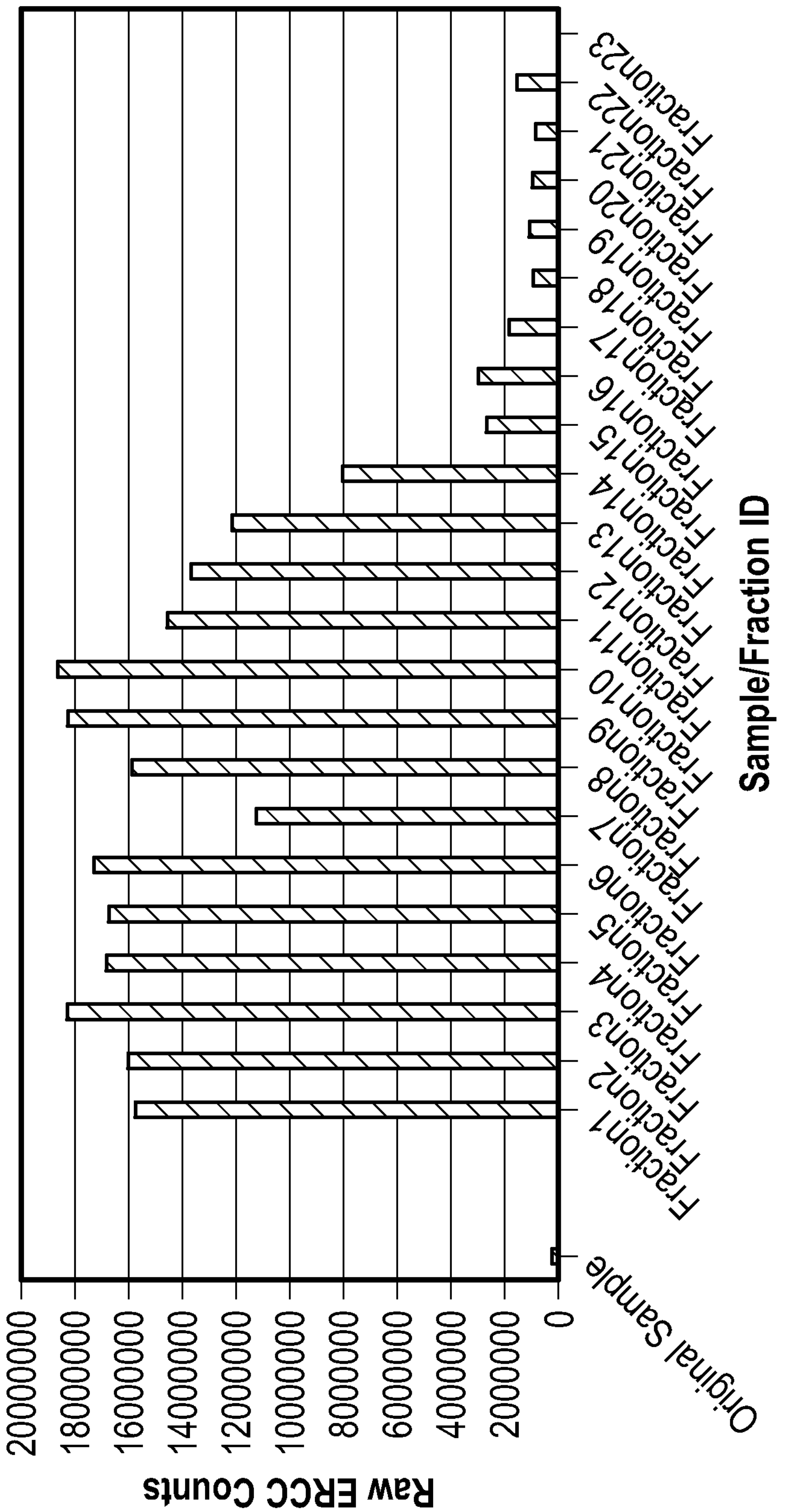
FIG. 8 is a bar graph diagram of raw internal standard ERCC counts of the original sample and the sample filtered into fractions 1-23 using liquid chromatography and then gene sequenced, in accordance with certain embodiments of the present invention.

The raw internal standard ERCC counts of the original sample and fractions 1-23 are illustrated in the bar graph provided in FIG. 8, which illustrates that fractionating of the liquid chromatography eluent is selecting for certain RNA. Up to fraction 14, the *Homo sapiens* fraction is relatively depleted.

Figure 9:
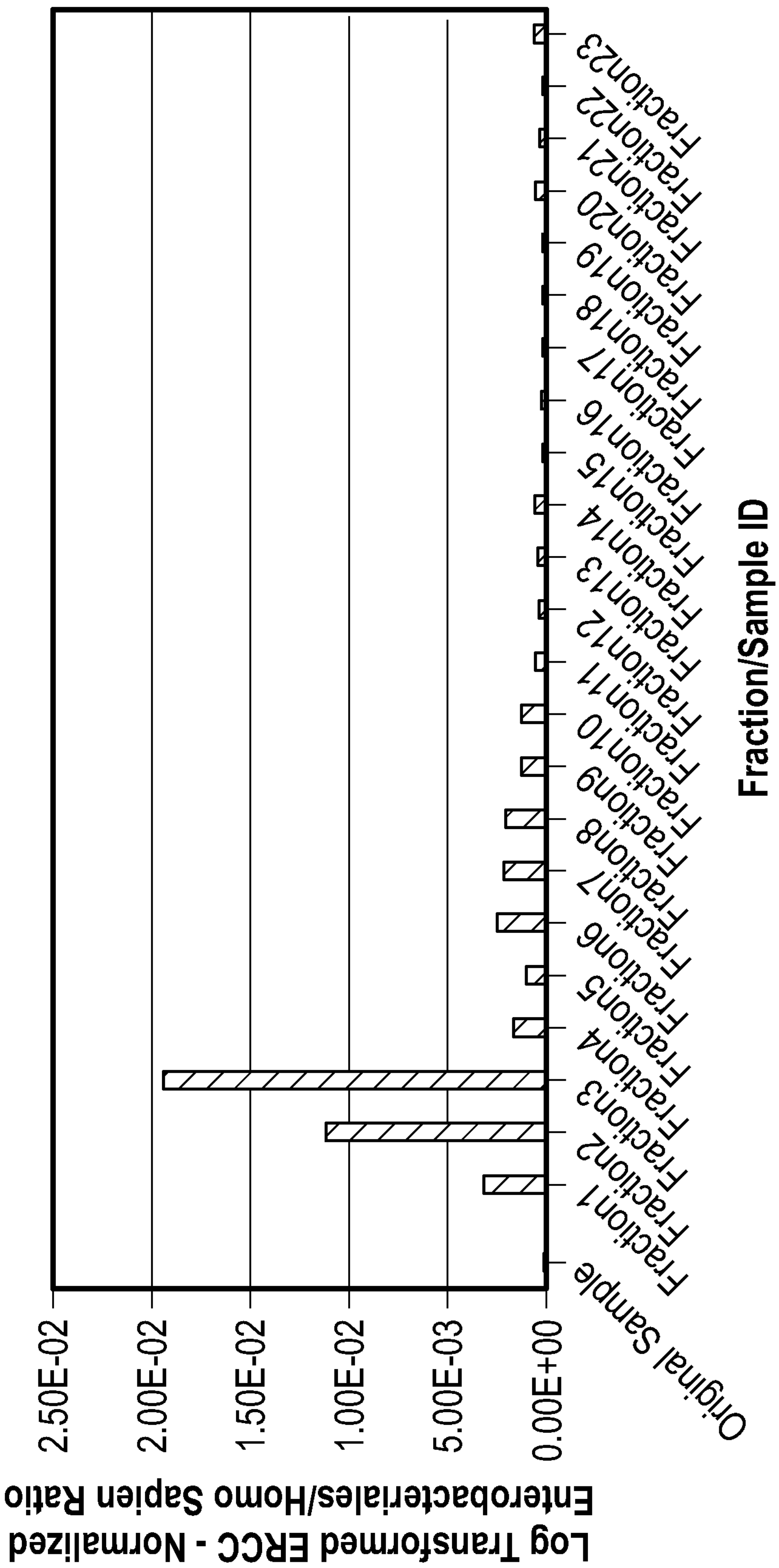
FIG. 9 is a bar graph diagram of Log Transformed ERCC-Normalized Enterobacteriales/*Homo sapiens* ratio of the original sample and the sample filtered into fractions 1-23 using liquid chromatography and then gene sequenced, in accordance with certain embodiments of the present invention.

Observed microbial and *Homo sapiens* annotation counts were normalized by observed ERCC sequence counts within each sample and were subsequently multiplied by a factor of 1,000,000. Calculated Enterobacteriales and *Homo sapiens* ERCC-normalized counts were then extracted to calculate a ratio of Enterobacteriales: *Homo sapiens* normalized counts within the original sample and each of fractions 1-23, as provided in FIG. 9. The bar graph of FIG. 9 illustrates the ratio of ERCC to *Homo sapiens* ratio throughout each of the fractions is filtering for microbial content, such that the liquid chromatograph is not excluding based upon microbial content.

Figure 10:
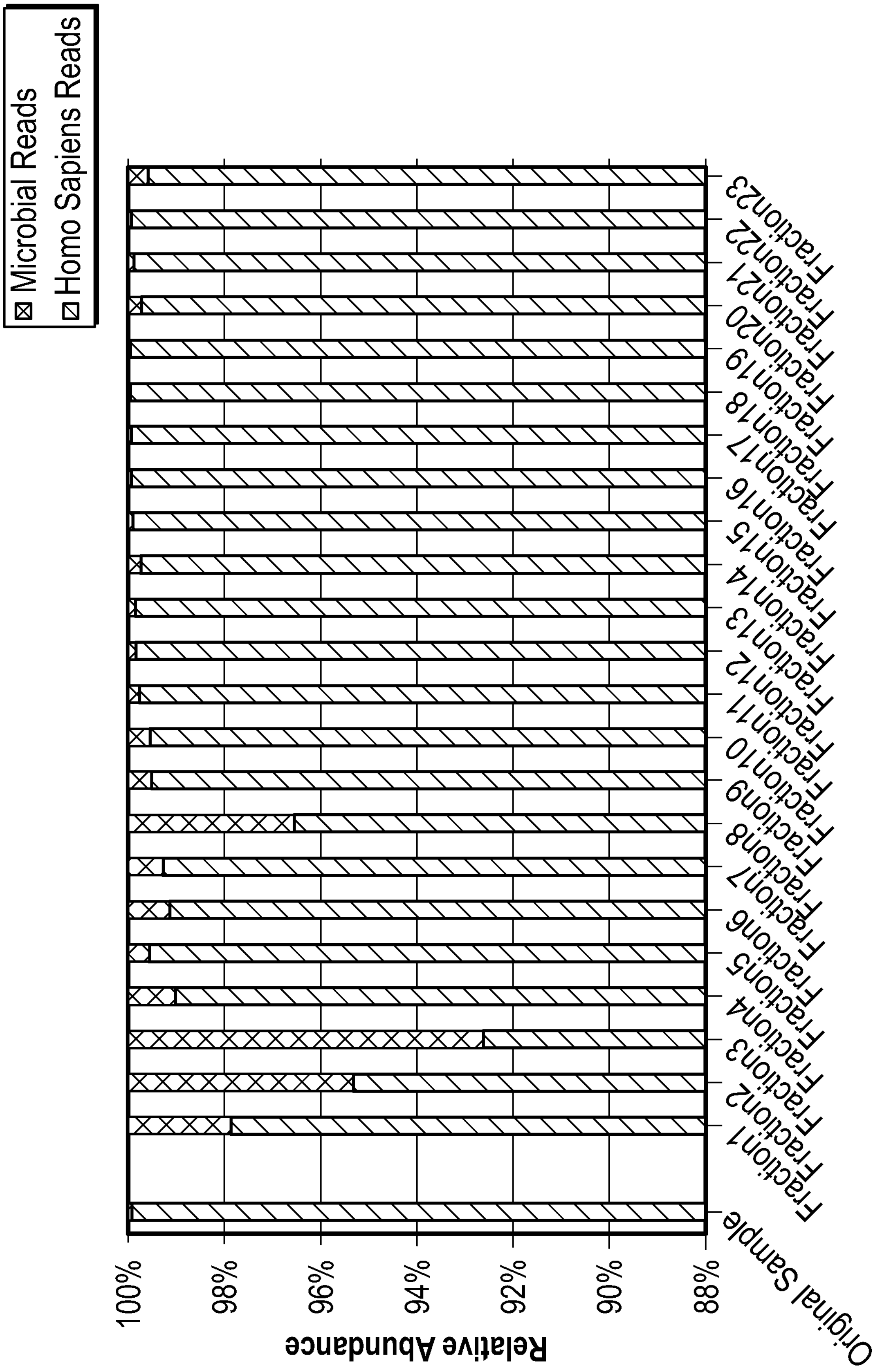
FIG. 10 is a bar graph diagram of the relative abundance of microbial reads and *Homo sapiens* reads of the original sample and the sample filtered into fractions 1-23 using liquid chromatography and then gene sequenced, in accordance with certain embodiments of the present invention.

The relative abundance of microbial reads (top portion of each bar) and *Homo sapiens* reads (bottom portion of each bar) of the original sample and fractions 1-23 is illustrated in the bar graph provided in FIG. 10. The distribution of annotated reads illustrates the relative amplification of the microbial reads in the void volume fractions. Specifically, about 5% of the reads of Fraction 2 and almost 8% of the reads in Fraction 3 are attributed to microbial reads (*E. coli* RNA), wherein the microbial reads in the original sample is about 0.03%. The void volume output of the liquid chromatography effectively amplifies the microbial RNA molecules from the test sample relative to the host RNA molecules by about 1/20 to about 1/10 in the void volume compared to 1/1,000,000 in the original sample. The effective amplification of the certain embodiments of the present method allows for RNA detection in the pictogram to nanogram range of genetic material.

EMBODIMENTS

The following embodiments are given only by way of example and are not intended to limit the scope of the claimed inventions as provided in the appended claims.

I. A method for filtering microbial RNA molecules from a biological specimen to isolate microbial RNA, the method comprising:

(a) obtaining the biological specimen;

(b) digesting the biological specimen to create a test sample by interacting a reagent with the specimen; and (c) using liquid chromatography to bulk filter microbial RNA molecules from a mixture of RNA molecules in the test sample to isolate and collect the microbial RNA molecules from the test sample.

II. The method of embodiment I, wherein the biological specimen is a mammalian specimen.

Ill. The method of embodiment I, wherein the biological specimen comprises one of at least of the following: large RNA molecules, small RNA molecules, tRNA molecules, rRNA molecules, mRNA molecules, denatured and non-denatured RNA molecules, microbial RNA molecules, non-microbial RNA molecules, genomic DNA molecules, protein molecules, and other macromolecules.

IV. The method of embodiment III, wherein the step of digesting the biological specimen removes genomic DNA molecules, protein molecules, and other macromolecules.

V. The method of embodiment I, wherein the microbial RNA molecules comprise fungal, viral, protozoa, amoebae, or bacterial RNA.

VI. The method of embodiment I, wherein the step of obtaining the biological specimen is performed in a clinical setting using at least one of a sterile technique or an antiseptic technique.

VII. The method of embodiment I, wherein the step of digesting the biological specimen uses a lysis reagent as the reagent.

VIII. The method of embodiment I, wherein the step of using liquid chromatography includes injecting the test sample into a sample port of a liquid chromatography instrument.

IX. The method of embodiment VIII, wherein the liquid chromatography instrument isolates the microbial RNA molecules by decreasing and then increasing an amount of an organic buffer in a mobile phase in relation to an aqueous buffer in the mobile phase.

X. The method of embodiment IX, wherein the amount of the organic buffer in the mobile phase is between 30% and 100%.

XI. The method of embodiment VIII, wherein the microbial RNA molecules are detected in the liquid chromatography instrument at a wavelength of 205 nm to 215 nm.

XII. The method of embodiment VIII, wherein the microbial RNA molecules are detected in the liquid chromatography instrument at a wavelength of 255 nm to 265 nm.

XIII. The method of embodiment VIII, wherein the microbial RNA molecules which the liquid chromatography instrument isolates are collected by diverting the mobile phase from a waste line.

XIV. The method of embodiment VIII, wherein a flow rate of the liquid chromatography instrument is 1 mL/min to 2.5 mL/min.

XV. The method of embodiment IX, wherein the aqueous buffer is comprised of one of at least 0.05M to 0.2M solution of triethylammonium acetate, phosphoric acid, citric acid, ammonium bicarbonate, formic acid, lactic acid, 2-[4-(2-hydroxyethyl)piperazin-1-yl]ethanesulfonic acid, maleic acid, diethanolamine, piperidine, ethanolamine, and triethanolamine.

XVI. The method of embodiment IX, wherein the organic buffer is comprised of a mixture of a 0.05M to 0.2 M aqueous buffer solution in one of at least 10% to 40% acetonitrile, methanol, ethanol, 1-propanol, 2-propanol, acetone, and tetrahydrofuran.

XVII. The method of embodiment VII, wherein the step of digesting the biological specimen comprises the steps of (a) lysing the biological specimen by interacting the biological specimen with one of at least Guanidinium thiocyanate, N-Lauroylsarcosine, and ethanol;

(b) washing the biological specimen by interacting the biological specimen with one of at least Guanidinium chloride, ethanol, 2-amino-2-(hydroxymethyl)-propane-1,3-dihydrochloride, and edetate disodium;

(c) cleaning the biological specimen by interacting the biological specimen with one of at least Proteinase K, Guanidinium thiocyanate, N-Lauroylsarcosine, ethanol, 2-amino-2-(hydroxymethyl) propane-1,3-dihydrochloride, and edetate disodium;

(d) isolating the test sample from the biological specimen by interacting the biological specimen with one of at least 55% to 85% Guanidinium thiocyanate, 1% to 20% N-Lauroylsarcosine, 70% to 100% ethanol, DNase I, 2-amino-2-(hydroxymethyl)-propane-1,3-dihydrochloride, and edetate disodium.

XVII. The method of embodiment XVII, wherein the step of lysing the biological specimen is completed by interacting the biological specimen with one of at least 55% to 85% Guanidinium thiocyanate, 1% to 20% N-Lauroylsarcosine, and 70% to 100% ethanol.

XIX. The method of embodiment XVII, wherein the step of washing the biological specimen is completed interacting the biological specimen with one of at least 25% to 55% Guanidinium chloride, 70% to 99% ethanol, 12 mg/m$^3$ to 790 mg/m$^3$ 2-amino-2-(hydroxymethyl) propane-1,3-dihydrochloride, and 20 mg/m$^3$ to 2,000 mg/m$^3$ edetate disodium.

XX. The method of embodiment XVII, wherein the step of cleaning the biological specimen is completed by interacting the clinical specimen with one of at least 4 U to 12 U Proteinase K, 55% to 85% Guanidinium thiocyanate, 1% to 20% N-Lauroylsarcosine, and 70% to 100% ethanol.

XXI. The method of embodiment XVII, wherein the step of isolating the test sample from the biological specimen is completed by interacting the biological specimen with one of at least 1 U to 15 U DNaseI, 25% to 85% Guanidinium thiocyanate, 1% to 20% N-Lauroylsarcosine, 70% to 100% ethanol, DNase I, 12 mg/m$^3$ to 790 mg/m$^3$ 2-amino-2-(hydroxymethyl)-propane-1,3-dihydrochloride, and 20 mg/m$^3$ to 2,000 mg/m$^3$ edetate disodium.

XXII. The method of embodiment XXI, wherein the step of isolating the test sample from the biological specimen is completed with a following step of at least one of boiling the test sample, treating the test sample with a denaturant, or storing the test sample. XXIII. The method of embodiment XXI, wherein the step of isolating the test sample from the clinical specimen is completed by boiling the test sample at 100'C to 120° C. for 10 minutes to 30 minutes.

XXIV. The method of embodiment XXII, wherein the step of treating the test sample with a denaturant is completed by interacting the test sample with 25% to 50% of one of at least polysorbate 20; polysorbate 80; (1,1,3,3-Tetramethylbutyl) phenyl-polyethylene glycol, Polyethylene glycol tert-octylphenyl ether; and 4-(1,1,3,3-Tetramethylbutyl)phenyl-polyethylene glycol, t-Octylphenoxypolyethoxyethanol, Polyethylene glycol tert-octylphenyl ether.

XXV. The method of embodiment VIII, wherein the microbial RNA molecules which the liquid chromatography instrument isolates are detected at elution times of 0 minutes to 3 minutes.

XXVI. A method of filtering a microbial single-stranded nucleic acid sequence from a mixture of one of at least a mammalian single-stranded nucleic acid sequence and a microbial single-stranded nucleic acid sequence by collecting microbial RNA molecules from a void volume of a liquid chromatography method, wherein the microbial single-stranded nucleic acid sequence is a catalyst for synthesis of a protein.

XXVII. The method of embodiment XXVI, wherein the void volume is represented by an initial time period in a chromatogram.

XXVIII. The method of embodiment XXVII, wherein the initial time period is 0 minutes to 6 minutes.

XXIX. The method of embodiment XXVIII, wherein the microbial RNA molecules in the void volume are positively charged.

XXX. The method of embodiment XXVIII, wherein the microbial RNA molecules in the void volume carry a net zero charge.

XXXI. The method of embodiment XXVIII, wherein the microbial RNA molecules in the void volume have a size of 1 nucleotide to 280 nucleotides.

XXXII. A method for filtering microbial RNA molecules from a biological specimen to isolate microbial RNA, the method comprising:

- obtaining the biological specimen;
- preparing the biological specimen to create a test sample by interacting a reagent with the specimen; and
- using a liquid chromatography instrument to bulk filter microbial RNA molecules from a mixture of RNA molecules in the test sample to isolate and collect the microbial RNA molecules from the test sample a void volume of the liquid chromatography instrument.

XXXIII. The method of embodiment XXXII, wherein the biological specimen is a mammalian specimen.

XXXIV. The method of embodiment XXXII, wherein the biological specimen comprises one of at least of the following: large RNA molecules, small RNA molecules, tRNA molecules, rRNA molecules, mRNA molecules, denatured and non-denatured RNA molecules, microbial RNA molecules, non-microbial RNA molecules, genomic DNA molecules, protein molecules, and other macromolecules.

XXXV. The method of embodiment XXXIIII, wherein the step of preparing the biological specimen purifies the specimen to change the relative characteristics of the genetic material.

XXXVI. The method of embodiment XXXV, wherein the step of preparing the biological specimen is substantially free of intentional growth of genetic material.

XXXVII. The method of embodiment XXXIV, wherein the step of preparing the biological specimen purifies the specimen to allow for filtration by liquid chromatography.

XXXVIII. The method of embodiment XXXIV, wherein the step of preparing the biological specimen purifies the specimen to remove genomic DNA molecules, protein molecules, and other macromolecules.

XXXIX. The method of embodiment XXXII, wherein the step of preparing the biological specimen has no intentional growth of genetic material.

XL. The method of embodiment XXXII, wherein the microbial RNA molecules comprise fungal, viral, protozoa, amoebae, or bacterial RNA.

XLI. The method of embodiment XXXII, wherein the step of obtaining the biological specimen is performed in a clinical setting using at least one of a sterile technique or an antiseptic technique.

XLII. The method of embodiment XXXII, wherein the step of digesting the biological specimen uses a lysis reagent as the reagent.

XLIII. The method of embodiment XXXII, wherein the step of using liquid chromatography includes injecting the test sample into a sample port of a liquid chromatography instrument.

XLIV. The method of embodiment XLIII, wherein the liquid chromatography instrument isolates the microbial RNA molecules by decreasing and then increasing an amount of an organic buffer in a mobile phase in relation to an aqueous buffer in the mobile phase.

XLV. The method of embodiment XLIV, wherein the amount of the organic buffer in the mobile phase is between 30% and 100%.

XLVI. The method of embodiment XLIII, wherein the microbial RNA molecules are detected in the liquid chromatography instrument at a wavelength of 205 nm to 215 nm.

XLVII. The method of embodiment XLIII, wherein the microbial RNA molecules are detected in the liquid chromatography instrument at a wavelength of 255 nm to 265 nm.

XLVIII. The method of embodiment XXXII, wherein the microbial RNA molecules which the liquid chromatography instrument isolates are collected in the void volume by diverting the mobile phase from a waste line.

As background and understanding of certain aspects of the present disclosure, reference is made to the following attachments which are hereby incorporated by reference:

1. Stewart, D. B.; Write, J. R.; Fowler, M.; McLimans, C. J.; Tokarev, V.; Amaniera, I.; Baker, O.; Wong, H.; Brabec, J.; Drucker, R.; Lamendella, R. "Integrated Meta Omics Reveals a Fungus-Associated Bacteriome and Distinct Functional Pathways in *Clostridioides difficile* Infection", Clinical Science and Epidemiology, 4(4), 1-16.
2. Goswami, K.; Purtill, J. J.; Shope, A. J.; Wright, J.; Lamendella, R. "Shotgun Metatranscriptomics for PJI diagnosis: A Novel Prospective Investigation, 2019 Abstract submission, AAHKS Annual Meeting.
3. Goswami, K.; Purtill, J. J.; Shope, A. J.; Wright, J.; Lamendella, R. "Shotgun Metatranscriptomics for PJI diagnosis: A Novel Prospective Investigation, 2019 Slide deck presentation, AAHKS Annual Meeting.
4. Slide deck for CSI Compendium, Confidential Investor Presentation, unpublished work (2019).

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

It should be noted that, as used in this specification and the appended claims, the singular forms "a", "an", and "the" include plural referents unless the content clearly indicates otherwise. Thus, for example, a clinical specimen containing "a microbial species" may include a mixture of two or more microbial species. It should also be noted that the term "or" is generally employed in its sense including "and/or" unless the content clearly dictates otherwise.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of U.S.C. § 112(f) are not to be invoked unless the specific terms "means for" or "step for" are recited in a claim.

The invention claimed is:

1. A method for enhancing the gene sequencing of microbial RNA molecules from a biological specimen, the method comprising:

(a) obtaining the biological specimen comprising the microbial RNA molecules;

(b) preparing the biological specimen as a test sample for high performance liquid chromatography (HPLC);

(c) using HPLC to bulk filter the microbial RNA molecules from a mixture of RNA molecules in the test sample to isolate and collect the microbial RNA molecules in two or more fraction outputs of the HPLC, wherein the collected microbial RNA molecules are single-stranded, and at least one of the two or more fraction outputs is a fraction output within a void volume of the HPLC;

(d) preparing the one or more fraction outputs for gene sequencing, wherein the one or more fraction outputs is the fraction output within the void volume, and wherein the fraction output comprises a ratio of microbial RNA to non-microbial RNA that is less than 1/1,000,000; and (e) conducting gene sequencing on the one or more prepared outputs to detect microbial RNA from the biological specimen.

2. The method of claim 1, wherein the biological specimen is a mammalian specimen.

3. The method of claim 1, wherein the biological specimen further comprises one or more of large RNA molecules, small RNA molecules, tRNA molecules, rRNA molecules, mRNA molecules, denatured and non-denatured RNA molecules, non-microbial RNA molecules, genomic DNA molecules, and protein molecules.

4. The method of claim 1, wherein preparing the biological specimen comprises digesting the biological specimen to create the test sample by interacting a reagent with the biological specimen.

5. The method of claim 4, wherein digesting the biological specimen comprises:

(i) adding to the biological specimen with one or more of Guanidinium thiocyanate, N-Lauroylsarcosine, and ethanol to create a lysed biological specimen;

(ii) washing the lysed biological specimen by combining the lysed biological specimen with one or more of Guanidinium chloride, ethanol, 2-amino-2-(hydroxymethyl)-propane -1,3-dihydrochloride, and edetate disodium to create a washed biological specimen;

(iii) cleaning the washed biological specimen by combining it with one or more of Proteinase K, Guanidinium thiocyanate, N-Lauroylsarcosine, ethanol, 2-amino-2-(hydroxymethyl) propane-1,3-dihydrochloride, and edetate disodium to create a cleaned biological specimen; and (iv) isolating the test sample from the washed biological specimen by combining it with one or more of 55% to 85% Guanidinium thiocyanate, 1% to 20% N-Lauroylsarcosine, 70% to 100% ethanol, DNase 1, 2-amino-2-(hydroxymethyl)-propane-1,3-dihydrochloride, and edetate disodium.

6. The method of claim 4, wherein digesting the biological specimen removes genomic DNA molecules, and protein molecules.

7. The method of claim 5, wherein lysing the biological specimen is completed by interacting the biological specimen with one or more of 55% to 85% Guanidinium thiocyanate, 1% to 20% N-Lauroylsarcosine, and 70% to 100% ethanol; wherein washing the biological specimen is completed by interacting the biological specimen with one or more of at least 25% to 55% Guanidinium chloride, 70% to 99% ethanol, 12 mg/m3 to 790 mg/m3 2-amino-2-(hydroxymethyl) propane-1,3-dihydrochloride, and 20 mg/m3 to 2,000 mg/m3 edetate disodium; wherein cleaning the biological specimen is completed by interacting the clinical specimen with one or more of 4U to 12U Proteinase K, 55% to 85% Guanidinium thiocyanate, 1% to 20% N-Lauroylsarcosine, and 70% to 100% ethanol; and wherein isolating the test sample from the biological specimen is completed by interacting the biological specimen with one or more of 1U to 15U DNase I, 55% to 85% Guanidinium thiocyanate, 1% to 20% N-Lauroylsarcosine, 70% to 100% ethanol, 12 mg/m3 to 790 mg/m3 2-amino-2-(hydroxymethyl)-propane -1,3-dihydrochloride, and 20 mg/m3 to 2,000 mg/m3 edetate disodium.

8. The method of claim 1, wherein the single-stranded microbial RNA molecules comprise one or more of fungal, viral, protozoa, amoebae, and bacterial RNA.

9. The method of claim 1, wherein the HPLC isolates the microbial RNA molecules by using a concentration gradient of an aqueous buffer in relation to an organic buffer in a mobile phase at a flow rate of between about 0.550 mL/min to about 2 mL/min.

10. The method of claim 9, wherein the aqueous buffer is comprised of one or more of 0.05M to 0.2M solution of treithylammonium acetate, phosphoric acid, citric acid, ammonium bicarbonate, formic acid, lactic acid, 2-[4-(2-hydroxyethyl) piperazin-1-yl]ethanesulfonic acid, maleic acid, diethanolamine, piperidine, ethanolamine, and triethanolamine.

11. The method of claim 9, wherein the organic buffer is comprised of a mixture of a 0.05M to 0.2M aqueous buffer solution in one or more of 10% to 40% acetonitrile, methanol, ethanol, 1-propanol, 2-propanol, acetone, and tetrahydrofuran.

12. The method of claim 1, wherein each of the two or more output fractions from the HPLC is collected for a period of time between about 10 seconds and about 45 seconds and has a volume between about 125 μL to about 750 μL.

13. The method of claim 1, wherein the microbial RNA molecules are filtered from a mixture of RNA molecules in the test sample using HPLC without incubation of the biological specimen.

14. The method of claim 1, wherein the microbial RNA molecules which the HPLC instrument isolates are detected in the void volume having an elution times of less than about 6 minutes or, less than about 4 minutes.

15. The method of claim 1, wherein preparing one or more fraction outputs for gene sequencing comprises:

(i) concentrating each of the one or more fraction outputs to provide one or more concentrated fraction outputs;

(ii) priming RNA material in each of the one or more concentrated fraction outputs to provide one or more primed RNA fraction outputs; and (iii) reverse-transcribing each of the one or more primed RNA fraction outputs into one or more cDNA fraction outputs.

* * * * *